[12] United States Patent  
Ohnuki et al.

[10] Patent No.: US 8,030,501 B2  
[45] Date of Patent: Oct. 4, 2011

(54) PROCESS FOR PRODUCING OPTICALLY ACTIVE 3-AMINO NITROGEN-CONTAINING COMPOUNDS

(75) Inventors: Masatoshi Ohnuki, Hyogo (JP); Masashi Izumida, Hyogo (JP); Akira Nishiyama, Hyogo (JP); Shingo Matsumoto, Hyogo (JP)

(73) Assignee: Kaneka Corporation, Osaka-Shi (JP)

( * ) Notice: Subject to any disclaimer, the term of this patent is extended or adjusted under 35 U.S.C. 154(b) by 142 days.

(21) Appl. No.: 12/375,141

(22) PCT Filed: Jul. 23, 2007

(86) PCT No.: PCT/JP2007/064406
§ 371 (c)(1),
(2), (4) Date: Apr. 17, 2009

(87) PCT Pub. No.: WO2008/013130
PCT Pub. Date: Jan. 31, 2008

(65) Prior Publication Data
US 2009/0326246 A1 Dec. 31, 2009

(30) Foreign Application Priority Data

Jul. 28, 2006 (JP) .................. 2006-205923
Jul. 28, 2006 (JP) .................. 2006-205926

(51) Int. Cl.
*C07D 295/00* (2006.01)
(52) U.S. Cl. .................................... 548/531
(58) Field of Classification Search .............. 548/531
See application file for complete search history.

(56) References Cited

U.S. PATENT DOCUMENTS 4,785,119 A 11/1988 Hojo et al.
5,977,381 A * 11/1999 Klinkhammer et al. ...... 548/557
6,140,347 A * 10/2000 Castro Pineiro et al. ..... 514/323

FOREIGN PATENT DOCUMENTS

| JP | 63-041452 | 2/1988 |
| JP | 02-218664 | 8/1990 |
| JP | 02-289568 | 11/1990 |
| JP | 02-290870 | 11/1990 |
| JP | 10-204086 | 8/1998 |
| JP | 2000-053642 | 2/2000 |
| JP | 2001-114759 | 4/2001 |
| JP | 2005-343835 | 12/2005 |
| JP | 2006-008518 | 1/2006 |

OTHER PUBLICATIONS

Cesare et al. (J. Med. Chem. 1992, 35, 4205-4213.*
Murphy et al (Organic Letter, 2005; 7 (15); 3287-3289).*
Vapor pressure of ethanol, which is available from the CRC Handbook of Chemistry and Physics, 44th ed—(years 1962-1963).*
DiCesare et al., J. Med. Chem., 35:4205-4213 (1992).
International Search Report in PCT/JP2007/064406 dated Oct. 9, 2007.
Sanchez et al., J. Med. Chem. 35:1764-1773 (1992).

* cited by examiner

*Primary Examiner* — Andrew D Kosar
*Assistant Examiner* — Valerie Rodriguez-Garcia
(74) *Attorney, Agent, or Firm* — Marshall, Gerstein & Borun LLP

(57) ABSTRACT

Aiming at production of an optically active 3-amino nitrogen-containing compound which is useful as an intermediate in synthesis of medicines and pesticides, in particular, an optically active 1-protected-3-aminopyrrolidine derivative, from an inexpensive and readily available raw material by a process which is efficient and can be practiced industrially, an optically active 3-amino nitrogen-containing compound is produced by performing a reaction of an optically active 3-substituted nitrogen-containing compound with ammonia, methylamine, ethylamine or dimethylamine in the presence of water. In addition, a 1-protected-3-aminopyrrolidine derivative is produced by performing a reaction of an optically active 1-protected-3-(sulfonyloxy)pyrrolidine derivative with ammonia, methylamine, ethylamine, or dimethylamine in the presence of methanol, ethanol, n-propanol, or isopropanol under a pressure of less than 30 barr.

19 Claims, No Drawings

US 8,030,501 B2

PROCESS FOR PRODUCING OPTICALLY ACTIVE 3-AMINO NITROGEN-CONTAINING COMPOUNDS

CROSS-REFERENCE TO RELATED APPLICATIONS

This is the U.S. national phase application of International Application No. PCT/JP2007/064406, filed Jul. 23, 2007, which claims the benefit of Japanese patent application No. 2006-205923, filed Jul. 28, 2006 and Japanese patent application No. 2006-205926, filed Jul. 28, 2006.

1. Technical Field

The present invention relates to a process for producing an optically active 3-amino nitrogen-containing compound which is useful as an intermediate in synthesis of medicines and pesticides, in particular, an optically active 1-protected-3-aminopyrrolidine derivative.

2. Background Art

Among the optically active 3-amino nitrogen-containing compounds, 1-protected-3-aminopyrrolidine derivatives having high optical purity have been reported to be particularly important as raw materials for manufacturing medicines and pesticides, for example, in Patent Document 1. Although a large number of processes for producing such compounds have been known, in particular, processes in which an optically active 3-hydroxypyrrolidine derivative which is inexpensive and industrially readily available is used as a starting raw material are one of the most efficient processes for production among all. Accordingly, examples of the process for producing an optically active 3-aminopyrrolidine derivative using an optically active 3-hydroxypyrrolidine derivative as a starting raw material are described below.

(1) A process for producing (S)-1-(tert-butoxycarbonyl)-3-aminopyrrolidine in which (R)-3-hydroxypyrrolidine hydrochloride is used as a starting substance, and after tert-butoxycarbonyl protection is carried out, the hydroxyl group is mesylated, followed by substitution with azido and subsequently allowing for catalytic reduction of the azido group (Patent Documents 2 and 3, Nonpatent Document 1).

(2) A process for producing optically active 1-(tert-butoxycarbonyl)-3-aminopyrrolidine in which optically active 3-hydroxypyrrolidine obtained by decarboxylation of optically active 4-hydroxyproline is protected with tert-butoxycarbonyl, and subsequently after a hydroxyl group at position 3 is mesylated, the product is subjected to azidation, and further catalytic reduction to produce corresponding optically active 1-(tert-butoxycarbonyl)-3-aminopyrrolidine (Patent Document 4).

(3) A process for producing (S)-1-(tert-butoxycarbonyl)-3-aminopyrrolidine in which (R)-3-hydroxypyrrolidine is protected with tert-butoxycarbonyl, and subsequently after a hydroxyl group at position 3 is mesylated, the product is allowed to react with liquid ammonia at 150° C. under a pressure of 132 barr to produce corresponding (S)-1-(tert-butoxycarbonyl)-3-aminopyrrolidine (Patent Document 5).

(4) A process for producing (R)-1-benzyl-3-(methylamino)pyrrolidine in which a hydroxyl group of (S)-1-benzyl-3-hydroxypyrrolidine is tosylated, and subsequently allowed to react with methylamine in ethanol at 140° C. for 20 hrs (Nonpatent Document 2).

(5) A process for producing (R)-1-(tert-butoxycarbonyl)-3-(methylamino)pyrrolidine in which after (S)-1-(tert-butoxycarbonyl)-3-(methanesulfonyloxy)pyrrolidine is allowed to react with N-benzylmethylamine, hydrogenolysis of a benzyl group is carried out in the presence of a palladium catalyst (Patent Document 6).

(6) A process for producing (R)-1-benzyl-3-aminopyrrolidine in which (S)-1-benzyl-3-hydroxypyrrolidine and phthalimide are coupled using a Mitsunobu reagent (diethyl azodicarboxylate and triphenylphosphine) to obtain a corresponding phthalimide form, which is then dephthalated with an acid aqueous solution (Patent Document 7).

Patent Document 1: Japanese Unexamined Patent Application, First Publication No. Hei 10-204086
Patent Document 2: Japanese Unexamined Patent Application, First Publication No. 2001-114759
Patent Document 3: Japanese Patent No. 2948857
Patent Document 4: Japanese Unexamined Patent Application, First Publication No. 2006-8518
Patent Document 5: Japanese Patent No. 3639449
Patent Document 6: U.S. Pat. No. 6,140,347
Patent Document 7: Japanese Unexamined Patent Application, First Publication No. Hei 2-290870
Nonpatent Document 1: J. Med. Chem., 1992, 35, 1764-1773
Nonpatent Document 2: J. Med. Chem., 1992, 35, 4205-4213

DISCLOSURE OF THE INVENTION

Problems to be Solved by the Invention

However, according to the above Prior Art process (1), practice on a commercial scale is difficult since: an azidating agent which is explosive and involves handling difficulties is used; further the reaction proceeds via thermally unstable 1-(tert-butoxycarbonyl)-3-azido-pyrrolidine as an intermediate; and purification is carried out in each step by a complicated operation with silica gel column chromatography. The Prior Art process (2) is not necessarily suited for industrial production since an azidating agent which is explosive and involves handling difficulties is used, and further the reaction proceeds via thermally unstable 1-(tert-butoxycarbonyl)-3-azido-pyrrolidine as an intermediate. According to the Prior Art process (3), practical application on an industrial scale can be hardly deemed to be versatile since liquid ammonia which has an extremely low boiling point and involves handling difficulties is used, and also the reaction is carried out under an ultra high pressure. In addition, also in the Prior Art process (4), the reaction is carried out at an ultra high temperature of 140° C. similarly to the Prior Art process (3), the reaction is speculated to be carried out under an ultra high pressure although no description with respect to the pressure is found. Furthermore, in the Prior Art process (5) expensive N-benzylmethylamine is used, and silica gel column chromatography is used in purification of the product; therefore, the process is not suited for industrially practical application. The Prior Art process (6) is also disadvantageous in use of diethyl azodicarboxylate accompanied by problems in connection with shock stability, and necessity to separate the product from waste materials such as triphenylphosphineoxide generated following the reaction as by-products.

Therefore, development of a process which can be practiced on an industrial scale, and can efficiently provide an optically active 3-amino nitrogen-containing compound with high quality has been demanded.

Means for Solving the Problems

In view of the foregoings, the present inventors elaborately investigated, and consequently found that in production of an optically active 3-amino nitrogen-containing compound by means of a reaction of an optically active 3-substituted nitrogen-containing compound with ammonia, methylamine, ethylamine or dimethylamine, the yield and the optical purity can be maintained, or further improved even under conditions of low temperature and low pressure by allowing water to coexist. In addition, it was also found that a 3-amino nitrogen-containing compound with further higher purity and higher optical purity is obtained by forming a salt from thus resulting optically active 3-amino nitrogen-containing compound and an acid, and crystallizing the salt from an organic solvent. Accordingly, the present invention was accomplished.

Moreover, the present inventors found that a 1-protected-3-aminopyrrolidine derivative with high optical purity can be obtained by allowing any one of methanol, ethanol, n-propanol, or isopropanol to coexist in allowing an optically active 1-protected-3-(sulfonyloxy)pyrrolidine derivative, which is readily available, to react with ammonia, methylamine, ethylamine, or dimethylamine, whereby the reaction proceeds efficiently even under a low pressure of less than 30 barr. Furthermore, it was also found that a 1-protected-3-aminopyrrolidine derivative with further higher purity and higher optical purity is obtained by forming a salt from thus resulting optically active 1-protected-3-aminopyrrolidine derivative and an acid, and then crystallizing the salt from an organic solvent. Thus, the present invention was accomplished.

Accordingly, a first aspect of the present invention provides a process for producing an optically active 3-amino nitrogen-containing compound represented by the following formula (2);

[chemical formula 1]

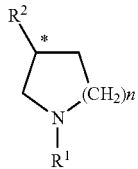

(2)

wherein, $R^1$ represents an alkyl group having 1 to 20 carbon atoms which may have a substituent, a cycloalkyl group having 3 to 20 carbon atoms which may have a substituent, an alkenyl group having 2 to 20 carbon atoms which may have a substituent, an aralkyl group having 7 to 20 carbon atoms which may have a substituent, an aryl group having 6 to 20 carbon atoms which may have a substituent, a heteroaryl group having 3 to 20 carbon atoms which may have a substituent, a hydroxyl group, an alkyloxy group having 1 to 20 carbon atoms, an aryloxy group having 6 to 20 carbon atoms, an aralkyloxy group having 7 to 20 carbon atoms, or a protecting group of an amino group; * represents an asymmetric carbon atom; n represents an integer of 1 to 3; and $R^2$ is an amino group, a methylamino group, an ethylamino group or a dimethylamino group, in which the position 3 is sterically inverted from the starting material, the process including allowing an optically active 3-substituted nitrogen-containing compound represented by the following formula (1);

[chemical formula 2]

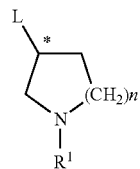

(1)

wherein, *, $R^1$ and n are as defined above; and L represents a leaving group, to react with ammonia, methylamine, ethylamine or dimethylamine in the presence of water.

Moreover, the first aspect of the present invention also provides a process for producing a salt of an optically active 3-amino nitrogen-containing compound including: forming a salt from an acid and the compound (2) produced by the aforementioned process; and crystallizing with an organic solvent, thereby obtaining the salt as a crystal while leaving contaminated impurities in the mother liquid.

A second aspect of the present invention provides a process for producing an optically active 1-protected-3-aminopyrrolidine derivative represented by the following formula (6);

[chemical formula 3]

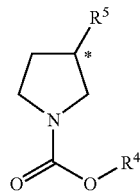

(6)

wherein $R^4$ represents an alkyl group having 1 to 20 carbon atoms which may have a substituent, an alkenyl group having 2 to 20 carbon atoms which may have a substituent, an aryl group having 6 to 20 carbon atoms which may have a substituent, or an aralkyl group having 7 to 20 carbon atoms which may have a substituent; * represents an asymmetric carbon atom; and $R^5$ is an amino group, a methylamino group, an ethylamino group, or a dimethylamino group, in which the position 3 is sterically inverted from the starting material, the process including allowing an optically active 1-protected-3-(sulfonyloxy)pyrrolidine derivative represented by the following formula (5);

[chemical formula 4]

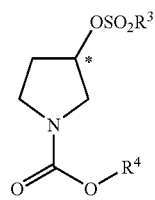

(5)

wherein, $R^3$ represents an alkyl group having 1 to 20 carbon atoms which may have a substituent, an aryl group having 6 to 20 carbon atoms which may have a substituent, or an aralkyl group having 7 to 20 carbon atoms which may have a substituent; and * and R⁴ are as defined above to react with ammonia, methylamine, ethylamine, or dimethylamine in the presence of at least one selected from the group consisting of methanol, ethanol, n-propanol and isopropanol under a pressure of less than 30 barr.

Moreover, the second aspect of the present invention also provides a process for producing a salt of an optically active 1-protected-3-aminopyrrolidine derivative including: forming a salt from an acid and the compound (6) produced by the aforementioned process; and crystallizing from an organic solvent, thereby obtaining the salt as a crystal while leaving contaminated impurities in the mother liquid.

Effects of the Invention

According to the present invention, production of an optically active 3-amino nitrogen-containing compound, particularly an optically active 1-protected-3-aminopyrrolidine derivative, with excellent quality (high purity, and high optical purity) in a convenient and efficient manner is enabled from an inexpensive and readily available raw material by a process which can be industrially practiced.

BEST MODE FOR CARRYING OUT THE INVENTION

First Aspect of the Present Invention

The raw (starting) material used in the first aspect of the present invention and the product are first explained.

In the present invention, the optically active 3-substituted nitrogen-containing compound is represented by the following formula (1):

[chemical formula 5]

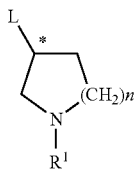

(1)

wherein, $R^1$ represents an alkyl group having 1 to 20 carbon atoms which may have a substituent, a cycloalkyl group having 3 to 20 carbon atoms which may have a substituent, an alkenyl group having 2 to 20 carbon atoms which may have a substituent, an aralkyl group having 7 to 20 carbon atoms which may have a substituent, an aryl group having 6 to 20 carbon atoms which may have a substituent, a heteroaryl group having 3 to 20 carbon atoms which may have a substituent, a hydroxyl group, an alkyloxy group having 1 to 20 carbon atoms, an aralkyloxy group having 7 to 20 carbon atoms, an aryloxy group having 6 to 20 carbon atoms, or a protecting of an amino group. As the alkyl group having 1 to 20 carbon atoms, for example, a methyl group, an ethyl group, a n-propyl group, an isopropyl group, a n-butyl group, a tert-butyl group, or the like may be exemplified; as the cycloalkyl group having 3 to 20 carbon atoms, for example, a cyclopropyl group, a cyclopentyl group, a cyclohexyl group, or the like may be exemplified; as the alkenyl group having 2 to 20 carbon atoms, for example, a vinyl group, an allyl group, a methallyl group, or the like may be exemplified; as the aralkyl group having 7 to 20 carbon atoms, for example, a benzyl group, a 1-phenethyl group, or the like may be exemplified; as the aryl group having 6 to 20 carbon atoms, for example, a phenyl group, a naphthyl group, a biphenyl group, or the like may be exemplified; as the heteroaryl group having 3 to 20 carbon atoms, for example, a pyridyl group, a furanyl group, a thienyl group, a pyrrolyl group, an oxazolyl group, an isooxazolyl group, a pyrazolyl group, a benzofuranyl group, a benzothiazolyl group, an indolyl group, or the like may be exemplified; as the alkyloxy group having 1 to 20 carbon atoms, for example, a methoxy group, an ethoxy group, an isopropoxy group, a tert-butoxy group, or the like may be exemplified; as the aralkyloxy group having 7 to 20 carbon atoms, for example, a benzyloxy group, a 1-phenethyloxy group, or the like may be exemplified; as the aryloxy group having 6 to 20 carbon atoms, for example, a phenoxy group, a biphenyloxy group or the like may be exemplified. As the substituent, for example, a halogen atom such as a fluorine atom, a chlorine atom, a bromine atom or an iodine atom, a nitro group, a nitroso group, a cyano group, an amino group, a hydroxyamino group, an alkylamino group having 1 to 12 carbon atoms, a dialkylamino group having 1 to 12 carbon atoms, an aralkylamino group having 7 to 12 carbon atoms, a diaralkylamino group having 7 to 12 carbon atoms, an alkylsulfonylamino group having 1 to 12 carbon atoms, a sulfonic acid group, a sulfoneamide group, an azido group, a trifluoromethyl group, a carboxyl group, an acyl group having 1 to 12 carbon atoms, an aroyl group having 7 to 12 carbon atoms, a hydroxyl group, an alkyloxy group having 1 to 12 carbon atoms, an aralkyloxy group having 7 to 12 carbon atoms, an aryloxy group having 6 to 12 carbon atoms, an acyloxy group having 1 to 12 carbon atoms, an aroyloxy group having 7 to 12 carbon atoms, a silyloxy group having 3 to 12 carbon atoms, an alkylsulfonyloxy group having 1 to 12 carbon atoms, an alkylthio group having 1 to 12 carbon atoms, or the like may be exemplified. Examples of the protecting group of the amino group include protecting groups of secondary amine described in JOHN WILEY & SONS, INC., "PROTECTIVE GROUPS in ORGANIC SYNTHESIS", Third edition, written by Theodora W. Greene, pp. 494 to 653, and specific examples thereof include alkyloxycarbonyl groups having 2 to 21 carbon atoms, aralkyloxycarbonyl groups having 8 to 21 carbon atoms, aryloxycarbonyl groups having 7 to 21 carbon atoms, and the like. $R^1$ is preferably a benzyl group, an allyl group, a hydroxyl group, an acetyl group, a benzoyl group, a methoxycarbonyl group, an ethoxycarbonyl group, an isopropoxy carbonyl group, a tert-butoxycarbonyl group, or a benzyloxycarbonyl group, and more preferably a benzyl group, a tert-butoxycarbonyl group, or a benzyloxycarbonyl group.

Herein, * represents an asymmetric carbon atom. Of two enantiomers, those including a slight amount of one enantiomer in excess are all involved in the present invention, however, in general, one having an optical purity of no less than 80% e.e., preferably no less than 90% e.e., and more preferably no less than 95% e.e. may be used as the compound (1).

Herein, L represents a leaving group. For example, an alkylsulfonyloxy group having 1 to 20 carbon atoms which may have a substituent, an arylsulfonyloxy group having 6 to 20 carbon atoms which may have a substituent, an aralkylsulfonyloxy group having 7 to 20 carbon atoms which may have a substituent, a halogen atom, or the like may be exemplified. Preferably, L may represent an alkylsulfonyloxy group having 1 to 20 carbon atoms which may have a substituent, an arylsulfonyloxy group having 6 to 20 carbon atoms which may have a substituent, or a chlorine atom. More preferably, L may represent a methanesulfonyloxy group, an ethanesulfonyloxy group, a trifluoromethanesulfonyloxy group, a benzenesulfonyloxy group, a p-methylbenzenesulfonyloxy group, a p-chlorobenzenesulfonyloxy group, an o-nitrobenzenesulfonyloxy group, a m-nitrobenzenesulfonyloxy group, a p-nitrobenzenesulfonyloxy group, or a chlorine atom, and particularly preferably a methanesulfonyloxy group.

Herein, n represents an integer of 1 to 3. Preferably, a pyrrolidine derivative in which n is 1, or a piperidine derivative in which n is 2, and more preferably, a pyrrolidine derivative in which n is 1 may be used.

With respect to availability of the compound (1), it may be produced by, for example, any of the processes described in Synlett, 1995, 1, 55-57., Bioorganic & Medicinal Chemistry Letters, 2000, 10 (21), 2417-2419., Japanese Patent No. 2948857, Japanese Patent No. 3639449, and the like.

Moreover, in the present invention, the optically active 3-amino nitrogen-containing compound is represented by the following formula (2).

[chemical formula 6]

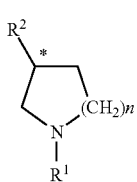

(2)

Herein, *, $R^1$ and n are as defined above. $R^2$ is an amino group, a methylamino group, an ethylamino group, or a dimethylamino group.

Next, the process for the production according to the first aspect of the present invention is explained.

More specifically, the optically active 3-amino nitrogen-containing compound represented by the above formula (2) is produced by allowing the optically active 3-substituted nitrogen-containing compound represented by the above formula (1) to react with ammonia, methylamine, ethylamine or dimethylamine in the presence of water. In this step, since the reaction proceeds along with inversion of the stereochemistry at position 3, a (R)-3-amino nitrogen-containing compound is formed from a (S)-3-substituted nitrogen-containing compound, while a (S)-3-amino nitrogen-containing compound is produced from a (R)-3-substituted nitrogen-containing compound.

Herein, the amount of ammonia, methylamine, ethylamine, or dimethylamine used may be preferably 5 to 300 times by mole, and more preferably 10 to 100 times by mole based on the mole of the compound (1). Moreover, the amount of water used may be preferably 0.1 to 10 times by weight, and more preferably 0.3 to 3 times by weight based on the weight of ammonia, methylamine, ethylamine, or dimethylamine. In other words, the concentration of ammonia, methylamine, ethylamine, or dimethylamine in the aqueous solution, which is derived from the foregoings, is preferably 9 to 91% by weight, and more preferably 25 to 77% by weight.

Furthermore, in the first aspect of the present invention, ammonia, methylamine, ethylamine, or dimethylamine may be used in an aqueous solution prepared beforehand. That is, ammonia (boiling point: −33° C.), methylamine (boiling point: −6° C.), ethylamine (boiling point: 17° C.), and dimethylamine (boiling point: 7° C.) are gaseous at around ordinary temperatures, and usually handled with being placed in a cylinder. Thus, a variety of restraints are forced as high pressure gases, in transport and storage, and upon use. In contrast, the aqueous solution of ammonia, methylamine, ethylamine, or dimethylamine is preferred since it is accompanied by less restraint in transport and storage, and also in light of ease in handling upon use.

In the reaction of the present invention, a reaction solvent is not particularly required as long as water is present in the reaction system, but a reaction solvent may be further added in the case in which the stirring is difficult due to low solubility of the substrate, or the like. Examples of the reaction solvent which can be used include e.g., alcoholic solvents such as methanol, ethanol, n-propanol, isopropanol, n-butanol, tert-butanol, and ethylene glycol; ether type solvents such as tetrahydrofuran, diethyl ether, 1,4-dioxane, and ethylene glycol dimethyl ether; aromatic hydrocarbon based solvents such as benzene, and toluene; aliphatic hydrocarbon based solvents such as pentane, hexane, heptane, and methylcyclohexane; halogen based solvents such as methylene chloride, 1,2-dichloroethane, and chlorobenzene; sulfoxide type solvents such as dimethyl sulfoxide; amide type solvents such as N,N-dimethylformamide, and N,N-dimethylacetamide; urea based solvents such as dimethylpropyleneurea; phosphonic triamide type solvents such as hexamethylphosphonic triamide; ketone type solvents such as acetone, and methyl ethyl ketone; and nitrile type solvents such as acetonitrile, and propionitrile. Preferably, an alcoholic solvent such as methanol, ethanol, n-propanol, isopropanol, 1-butanol, tert-butanol, or ethylene glycol may be used. These may be used alone, or two or more of them may be used in combination. When two or more of them are used in combination, the mixing ratio is not particularly limited. The amount of the reaction solvent is preferably no more than 50 times by weight, and more preferably no more than 20 times by weight based on the weight of the compound (1), because of disadvantages in terms of cost and post processing when too much solvent is used.

The pressure in the present reaction closely correlates to the reaction rate and the optical purity (racemization) of the product, and thus is very important. Although the higher reaction pressure is advantageous since the reaction rapidly proceeds and the optical purity can be maintained (capable of inhibiting racemization), it may be difficult to practice on an industrial scale under a pressure of a certain level or higher because a special equipment is required. The preferable pressure according to the present invention may be less than 30 barr which can be generally practiced industrially, more preferably less than 20 barr, and particularly preferably less than 10 barr. The lower limit of the pressure is not particularly limited, and is preferably ambient pressure or higher.

The temperature in the present reaction may be predetermined ad libitum depending on the concentration of the aqueous solution of the ammonia, methylamine, ethylamine, or dimethylamine used, as well as the upper limit pressure of the reaction equipment. The temperature is preferably less than 100° C., and more preferably 40 to 90° C. The reaction time may be also predetermined ad libitum depending on the equivalence of the ammonia, methylamine, ethylamine, or dimethylamine used, as well as the upper limit pressure and the reaction temperature, and is preferably 1 to 48 hrs and more preferably 3 to 24 hrs.

The order of addition of the reagents in the present reaction is not particularly limited, and may be arbitrarily determined.

According to the present reaction, the compound (2) can be produced while inhibiting racemization in the state in which the optical purity of the compound (1) is maintained. Since the racemization is inhibited, and thus the optical purity is hardly reduced, the compound (2) having an optical purity of no less than 80% e.e., preferably no less than 90% e.e., and more preferably no less than 95% e.e., in general, can be produced depending on the optical purity of the compound (1).

As the post processing following the reaction, any of general treatments for obtaining the product from the reaction mixture may be carried out. For example, the ammonia, methylamine, ethylamine, or dimethylamine may be removed by distillation from the reaction mixture after completing the reaction by an operation such as heating under reduced pressure; and an extraction operation may be conducted after adding an aqueous alkali solution such as an aqueous sodium hydroxide solution or an aqueous sodium bicarbonate solution to the residue as needed, and then adding a general extraction solvent, such as e.g., ethyl acetate, diethyl ether, toluene, hexane, methylene chloride or the like. The compound (2) can be obtained by removing the reaction solvent and the extraction solvent by distillation from the extraction liquid through an operation such as heating under reduced pressure. The compound (2) obtained in such a manner may include at least one from among the compound (1), an enantiomer of and the compound (2), and a 3-hydroxy nitrogen-containing compound represented by the following formula (3);

[chemical formula 7]

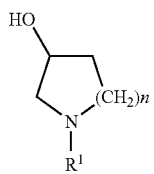

(3)

(wherein, $R^1$ and n are as defined above), and a dehydro nitrogen-containing compound represented by the following formula (4);

[chemical formula 8]

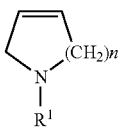

(4)

(wherein, $R^1$ and n are as defined above), as impurities. Next, since the yield achieved in the following step, or the purity of the compound obtained in the following step may be reduced when the resultant mixture is used in the following step, the process for removing these impurities are explained below.

More specifically, by forming a salt from the compound (2) and an acid, and then crystallizing with an organic solvent, the salt can be obtained as a crystal while the contaminated impurities are left in the mother liquid.

Herein, examples of the acid include e.g., inorganic acids such as hydrogen fluoride, hydrogen chloride, hydrogen bromide, hydrogen iodide, sulfuric acid, nitric acid, phosphoric acid, and boric acid; carboxylic acids such as formic acid, acetic acid, propionic acid, butyric acid, pivalic acid, chloroacetic acid, trichloroacetic acid, trifluoroacetic acid, oxalic acid, L-tartaric acid, D-tartaric acid, and mandelic acid; and sulfonic acids such as methanesulfonic acid, trifluoromethanesulfonic acid, benzenesulfonic acid, p-toluenesulfonic acid, and camphorsulfonic acid. The acid may be preferably hydrogen chloride, hydrogen bromide, sulfuric acid, acetic acid, pivalic acid, oxalic acid, L-tartaric acid, D-tartaric acid, mandelic acid, methanesulfonic acid, p-toluenesulfonic acid, or camphorsulfonic acid, and more preferably hydrogen chloride, hydrogen bromide, acetic acid, methanesulfonic acid, or p-toluenesulfonic acid. The amount of the acid is preferably 0.5 to 5 times by mole, and more preferably 0.5 to 1.5 times by mole based on the mole of the compound (2).

Examples of the organic solvent which can be used include e.g., alcoholic solvents such as methanol, ethanol, n-propanol, isopropanol, n-butanol, tert-butanol, and ethylene glycol; ester type solvents such as ethyl acetate, n-propyl acetate, and isopropyl acetate; ether type solvents such as tetrahydrofuran, diethyl ether, 1,4-dioxane, methyl tert-butyl ether, and ethylene glycol dimethyl ether; ketone type solvents such as acetone, and methyl ethyl ketone; nitrile type solvents such as acetonitrile, and propionitrile; aromatic hydrocarbon based solvents such as benzene, and toluene; aliphatic hydrocarbon based solvents such as pentane, hexane, heptane, and methylcyclohexane; halogen based solvents such as methylene chloride, 1,2-dichloroethane, and chlorobenzene; sulfoxide type solvents such as dimethyl sulfoxide; amide type solvents such as N,N-dimethylformamide, and N,N-dimethylacetamide; urea based solvents such as dimethylpropyleneurea; and phosphonic triamide type solvents such as hexamethylphosphonic triamide. The organic solvent may be preferably methanol, ethanol, isopropanol, ethyl acetate, n-propyl acetate, isopropyl acetate, tetrahydrofuran, methyl tert-butyl ether, acetone, acetonitrile, toluene, hexane, heptane, or methylcyclohexane, and more preferably isopropanol, ethyl acetate, or toluene. These may be used alone, or two or more of them may be used in combination. When two or more of them are used in combination, the mixing ratio is not particularly limited. The amount of the organic solvent is preferably no more than 50 times by weight, and more preferably no more than 20 times by weight based on the weight of the compound (2), because of disadvantages in terms of cost and post processing when too much solvent is used.

Although the process for the crystallization with the organic solvent in this step is not particularly limited, for example, the following process may be exemplified.

(a) A process for crystallization by mixing the compound (2) with an aqueous solution of the acid, or with the acid and water in an organic solvent, and thereafter concentrating the mixture and removing the moisture by distillation. In this instance, an organic solvent azeotropic with water (for example, ethanol, isopropanol, ethyl acetate, toluene or the like) may be used, whereby the azeotropic effect can be utilized in removing the moisture by distillation.

(b) A process for crystallization by mixing the compound (2) with the acid in an organic solvent.

(c) A process for crystallization by mixing the compound (2) with the acid in an organic solvent, and thereafter cooling.

The process for crystallization described above may be appropriately selected depending of the type of the acid, and the combination with the organic solvent. For example, in the case of hydrogen chloride or hydrogen bromide, since hydrochloric acid or hydrobromic acid, i.e., the aqueous solution thereof, can be more easily handled, the process (a) may be suited. To the contrary, in the case of use of an acid such as methanesulfonic acid or acetic acid which can be easily used generally as a nonhydrate, the process (b) is preferably selected. Alternatively, the salt obtained in the process (a), (b) or (c) may be used in combination with any of the crystallization processes of the following (d) to (f), or the salt obtained in the process (a), (b) or (c) may be dissolved in an organic solvent and may further subjected to any of the crystallization processes of (d) to (f). As would be apparent, the processes for crystallization (d) to (f) may be carried out repeatedly.

(d) A process of crystallization in which a salt of the compound (2) dissolved in an organic solvent is cooled.

(e) A process of crystallization in which a poor solvent is added to, or a poor solvent is used for enrichment and substitution of, the organic solvent including the salt of the compound (2) dissolved therein.

(f) A process of crystallization in which the salt of the compound (2) is dissolved in an organic solvent, and thereafter other acid is added.

As described above, the process (a), (b), (c), (d), (e) or (f) may be used in combination appropriately to permit crystallization.

As the organic solvent used in the process of crystallization, those similar to the organic solvents described above may be exemplified, and examples of the poor solvent which may be used in the process (e) include e.g., toluene, hexane, and the like. Moreover, a seed crystal may be added in crystallization.

The temperature in carrying out the processes of crystallization (a) to (f) is not particularly limited, and may be selected ad libitum depending on the type of the salt and the type of the solvent employed. Preferably, the temperature may be preset depending on the amount of the intended precipitate and the quality of the crystal within the range below the temperature at which the salt of the compound (2) is dissolved in the solvent or mixed solvent of the employed type.

The salt of the compound (2) precipitated in the processes of crystallization (a) to (f) can be separated and obtained by the procedure such as vacuum filtration, compression filtration, or centrifugation. In addition, when the purity of the crystal is deteriorated due to the remaining mother liquid in thus obtained crystal, the quality can be improved by further washing with an organic solvent as needed.

The drying of the crystal may be desirably carried out by a procedure of drying under reduced pressure (vacuum drying) at about no higher than 60° C., so as to avoid thermal decomposition and melting.

Since the aforementioned impurities can be removed by carrying out the process of crystallization, the chemical purity of the salt of the compound (2) is improved, and improvement of the optical purity is also enabled.

The salt of the compound (2) obtained by the aforementioned method can be further subjected to a treatment with a base such as an alkali metal hydroxide to release the compound (2), followed by operation such as extraction, concentration and the like, whereby the compound (2) having improved chemical purity can be also obtained.

Second Aspect of the Present Invention

The raw material used in the second aspect of the present invention, and the product are first explained.

In the present invention, the optically active 1-protected-3-(sulfonyloxy)pyrrolidine derivative is represented by the following formula (5).

[chemical formula 9]

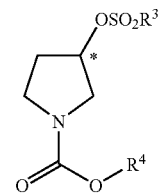

(5)

Wherein, $R^3$ represents an alkyl group having 1 to 20 carbon atoms which may have a substituent, an aryl group having 6 to 20 carbon atoms which may have a substituent, or an aralkyl group having 7 to 20 carbon atoms which may have a substituent. As the alkyl group having 1 to 20 carbon atoms, for example, a methyl group, an ethyl group, a n-propyl group, an isopropyl group, a n-butyl group, a tert-butyl group, or the like may be exemplified; as the aryl group having 6 to 20 carbon atoms, for example, a phenyl group, a p-methylphenyl group, a naphthyl group, a biphenyl group, or the like may be exemplified; and as the aralkyl group having 7 to 20 carbon atoms, for example, a benzyl group, a 1-phenethyl group, or the like may be exemplified. As the substituent, for example, a halogen atom such as a fluorine atom, a chlorine atom, a bromine atom or an iodine atom, a nitro group, a nitroso group, a cyano group, an amino group, a hydroxyamino group, an alkylamino group having 1 to 12 carbon atoms, a dialkylamino group having 1 to 12 carbon atoms, an aralkylamino group having 7 to 12 carbon atoms, a diaralkylamino group having 7 to 12 carbon atoms, an alkylsulfonylamino group having 1 to 12 carbon atoms, a sulfonic acid group, a sulfoneamide group, an azido group, a trifluoromethyl group, a carboxyl group, an acyl group having 1 to 12 carbon atoms, an aroyl group having 7 to 12 carbon atoms, a hydroxyl group, an alkyloxy group having 1 to 12 carbon atoms, an aralkyloxy group having 7 to 12 carbon atoms, an aryloxy group having 6 to 12 carbon atoms, an acyloxy group having 1 to 12 carbon atoms, an aroyloxy group having 7 to 12 carbon atoms, a silyloxy group having 3 to 12 carbon atoms, an alkylsulfonyloxy group having 1 to 12 carbon atoms, an alkylthio group having 1 to 12 carbon atoms, or the like may be exemplified. $R^3$ is preferably a methyl group, an ethyl group, a trifluoromethyl group, a p-methylphenyl group, or a p-chlorophenyl group, more preferably a methyl group, or a p-methylphenyl group, and particularly preferably a methyl group.

$R^4$ represents an alkyl group having 1 to 20 carbon atoms which may have a substituent, an alkenyl group having 2 to 20 carbon atoms which may have a substituent, an aryl group having 6 to 20 carbon atoms which may have a substituent, or an aralkyl group having 7 to 20 carbon atoms which may have a substituent. Specific examples of the alkyl group having 1 to 20 carbon atoms, the aryl group having 6 to 20 carbon atoms, and the aralkyl group having 7 to 20 carbon atoms include those described above. As the alkenyl group having 2 to 20 carbon atoms, for example, a vinyl group, an allyl group, a methallyl group, or the like may be exemplified. Specific examples of the substituent include those described above. $R^4$ is preferably a methyl group, a chloromethyl group, an ethyl group, a n-propyl group, an isopropyl group, a tert-butyl group, an allyl group, a phenyl group, or a benzyl group, more preferably a methyl group, an ethyl group, a n-propyl group, an isopropyl group, a tert-butyl group, or a benzyl group, and particularly preferably a tert-butyl group.

Herein, * represents an asymmetric carbon atom. Of two enantiomers, those including a slight amount of one enantiomer in excess are all involved in the present invention, however, in general, one having an optical purity of no less than 80% e.e., preferably no less than 90% e.e., and more preferably no less than 95% e.e. may be used as the compound (5).

The route for obtaining the compound (5) is not particularly limited. Specifically, for example, in addition to the process described below, the processes disclosed in Japanese Patent No. 2948857 and Japanese Patent No. 3639449, and the like may be involved.

Moreover, in the present invention, the optically active 1-protected-3-aminopyrrolidine derivative is represented by the following formula (6):

[chemical formula 10]

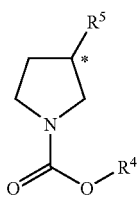

(6)

wherein, * and $R^4$ are as defined above; and $R^5$ is an amino group, a methylamino group, an ethylamino group, or a dimethylamino group.

Further, in the present invention, a 1-benzyl-3-(sulfonyloxy)pyrrolidine derivative is represented by the following formula (7).

[chemical formula 11]

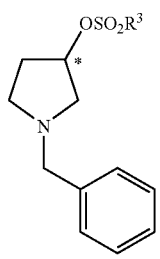

(7)

Herein, $R^3$ and * are as defined above. The compound (7) can be produced by allowing optically active 1-benzyl-3-hydroxypyrrolidine to react with a sulfonylating agent in the presence of a base. For example, it can be produced by allowing to react with a sulfonylating agent such as methanesulfonyl chloride or p-toluenesulfonyl chloride using sodium hydroxide as a base in a two-layer reaction system of an organic solvent and water according to the process disclosed in pamphlet of WO No. 01/94304.

Next, the process for production according to the second aspect of the present invention is explained. First, the step for producing the optically active 1-protected-3-(sulfonyloxy) pyrrolidine derivative represented by the above formula (5) is explained.

Although the process for producing the compound (5) is not particularly limited, for example, the benzyl group of the compound (7) is deprotected beforehand by catalytic reduction, and subsequently carbamate protection on the nitrogen atom may be conducted using a carbamating agent in the coexistence of a base. Alternatively, the compound represented by the above formula (7) can be also produced by carrying out catalytic reduction in the presence of an acid anhydride represented by the following formula (8):

[chemical formula 12]

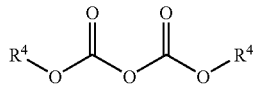

(8)

(wherein, $R^4$ is as defined above). The catalytic reduction of the compound represented by the above formula (7) which is carried out in the presence of the acid anhydride represented by the above formula (8) is preferred since deprotection of the benzyl group and carbamate protection can be performed concomitantly, whereby extremely advantageous industrial production is enabled because of reduction of additional reagents, shortening of the reaction time, increase in the yield, and the like.

The process for concomitantly performing the deprotection of the benzyl group and carbamate protection by the catalytic reduction of the compound represented by the above formula (7) in the presence of the acid anhydride represented by the above formula (8) is explained below. As the process for the catalytic reduction, a process in which hydrogenation is carried out in the presence of a transition metal catalyst may be exemplified. As the transition metal catalyst, for example, platinum, rhodium, palladium, nickel, ruthenium, iridium, or rhenium may be exemplified, and specific examples include metals such as platinum, rhodium, palladium, nickel, ruthenium, iridium and rhenium, alloys, and chloride thereof, and the like. Further, as such catalysts, those dispersed in a powder support are more preferably used in light of catalytic activity, reproducibility, storage stability, operation performance, and recycling. As the powder support, for example, carbon, alumina, silica-alumina, silica, barium carbonate, barium sulfate, calcium carbonate, titanium oxide, zirconium oxidize, zeolite, asbestos, or the like may be exemplified. Preferably, a metal such as platinum, rhodium, or palladium, or sulfide or hydroxide of the same carried by such a powder support may be used. Specific examples include e.g., platinum-carbon, platinum (II) sulfide-carbon, platinum-alumina, platinum-silica-alumina, platinum-silica, platinum-barium carbonate, platinum-barium sulfate, platinum-calcium carbonate, platinum-titanium oxide, platinum-zirconium oxide, platinum-zeolite, platinum-asbestos, platinum rhodium alloy-carbon, platinum palladium alloy-carbon, rhodium-carbon, rhodium-alumina, rhodium-silica, rhodium-calcium carbonate, palladium-carbon, palladium hydroxide (II)-carbon, palladium (II) sulfide-carbon, palladium-alumina, palladium-silica-alumina, palladium-silica, palladium-barium carbonate, palladium-barium sulfate, palladium-calcium carbonate, palladium-titanium oxide, palladium-zirconium oxide, palladium-zeolite, palladium-asbestos, ruthenium-carbon, ruthenium-alumina, ruthenium-silica, ruthenium-calcium carbonate, iridium-carbon, iridium-alumina, iridium-silica, iridium-calcium carbonate and the like. Preferably, palladium-carbon, rhodium-carbon, platinum-carbon or palladium hydroxide (II)-carbon, and more preferably, palladium-carbon may be used. These transition metal catalysts may be used alone, or two or more may be used in combination. The amount of the transition metal catalyst included is preferably no more than 5 times by weight, and more preferably 0.01 to 0.5 times by weight based on the weight of the compound (7) since too large amount is not preferred in terms of the cost and the post processing.

The acid anhydride represented by the above formula (8) is preferably dimethyl dicarbonate, diethyl dicarbonate, di n-propyl dicarbonate, diisopropyl dicarbonate, di tert-butyl dicarbonate, or dibenzyl dicarbonate, and more preferably di tert-butyl dicarbonate. The amount of the compound (8) used is preferably 1 to 10 times by mole, and more preferably 1 to 2 times by mole based on the mole number of the compound (7).

The reaction temperature of this reaction is preferably −20 to 100° C., and more preferably 0 to 50° C. The hydrogen pressure in this reaction is preferably no greater than 50 barr, and more preferably 1 to 10 barr.

The solvent in this reaction is not particularly limited as long as it does not affect the reaction, and for example, water; an alcoholic solvent such as methanol, ethanol, n-propanol, isopropanol, n-butanol, tert-butanol, or ethylene glycol; an ether type solvent such as tetrahydrofuran, diethyl ether, 1,4-dioxane, methyl tert-butyl ether, or ethylene glycol dimethyl ether; an aromatic hydrocarbon based solvent such as benzene, or toluene; an aliphatic hydrocarbon based solvent such as pentane, hexane, heptane, or methylcyclohexane, or the like may be employed. Preferably, an alcoholic solvent such as methanol, ethanol, n-propanol, isopropanol, n-butanol, tert-butanol, or ethylene glycol; an aromatic hydrocarbon based solvent such as benzene, or toluene, and more preferably methanol or toluene may be employed. These may be used alone, or two or more of them may be used in combination. When two or more of them are used in combination, the mixing ratio is not particularly limited. The amount of the solvent is preferably no more than 50 times by weight, and more preferably no more than 20 times by weight based on the weight of the compound (7), because of disadvantages in terms of cost and post processing when too much solvent is used.

The reaction temperature is not particularly limited, and may be preset appropriately. However, in order to reduce production of the by-product, the reaction temperature is preferably −20 to 100° C., and more preferably 0 to 50° C. Furthermore, the reaction time may be preset ad libitum depending on the amount of the catalyst used, and the upper limit pressure of the reaction equipment, which is preferably 1 to 24 hrs, and more preferably 3 to 12 hrs.

Upon the reaction, the procedures for adding the compound (7), the compound (8), the transition metal catalyst, and hydrogen are not particularly limited. The order of the addition is not particularly limited as long as hydrogen is finally added.

As the post processing following the reaction, general treatment for obtaining a product from the reaction mixture may be conducted. For example, the desired product may be obtained by filtrating off the catalyst from the reaction mixture after completing the reaction, and then removing by distillation of the reaction solvent from the filtrate according to an operation such as heating under reduced pressure. Although the desired product obtained in such a manner has a purity satisfactory for enabling use in the following step, in attempts for further improving the purity, general purification procedure such as crystallization, fractional distillation, column chromatography and the like may be carried out to achieve high purity.

Next, the step in producing the optically active 1-protected-3-aminopyrrolidine derivative represented by the above formula (6) by allowing the optically active 1-protected-3-(sulfonyloxy)pyrrolidine derivative represented by the above formula (5) to react with ammonia, methylamine, ethylamine, or dimethylamine is explained. In this step, since the reaction proceeds along with inversion of the stereochemistry at position 3, a (R)-1-protected-3-aminopyrrolidine derivative is formed from a (S)-1-protected-3-(sulfonyloxy)pyrrolidine derivative, while a (S)-1-protected-3-aminopyrrolidine derivative is formed from a (R)-1-protected-3-(sulfonyloxy) pyrrolidine derivative. This step is characterized by enabling the compound (6) to be obtained with high optical purity at a high yield, even under a comparatively low pressure of less than 30 barr by allowing at least one selected from the group consisting of methanol, ethanol, n-propanol and isopropanol to coexist in the reaction system.

Herein, the amount of ammonia, methylamine, ethylamine, or dimethylamine may be preferably 5 to 300 times by mole, and more preferably 10 to 100 times by mole based on the mole of the compound (5). Also, the methanol, ethanol, n-propanol, or isopropanol to be present in the reaction system may be used alone, or two or more may be used in combination. When two or more of them are used in combination, the mixing ratio is not particularly limited. The amount of the methanol, ethanol, n-propanol, or isopropanol may be preferably 0.1 to 10 times by weight, and more preferably 0.3 to 3 times by weight based on the weight of the aforementioned ammonia, methylamine, ethylamine, or dimethylamine. In other words, the concentration of ammonia, methylamine, ethylamine, or dimethylamine, which is derived from the foregoings, is preferably 9 to 91% by weight, and more preferably 25 to 77% by weight.

Furthermore, in the second aspect of the present invention, ammonia, methylamine, ethylamine, or dimethylamine may be used in an alcoholic solution prepared beforehand. That is, ammonia (boiling point: −33° C.), methylamine (boiling point: −6° C.), ethylamine (boiling point: 17° C.), and dimethylamine (boiling point: 7° C.) are gaseous at around ordinary temperatures, and usually handled with being placed in a cylinder. Thus, a variety of restraints are forced as high pressure gases, in transport and storage, and upon use. In contrast, the alcoholic solution of ammonia, methylamine, ethylamine, or dimethylamine is preferred since it is accompanied by less restraint in transport and storage, and also in light of ease in handling upon use.

In the reaction of the present invention, as long as at least one solvent selected from the group consisting of methanol, ethanol, n-propanol and isopropanol is present, any other additional reaction solvent is not particularly required, but a reaction solvent may be further added in the case in which the stirring is difficult due to low solubility of the substrate, or the like. Examples of the reaction solvent which can be used include e.g., ether type solvents such as tetrahydrofuran, diethyl ether, 1,4-dioxane, and ethylene glycol dimethyl ether; aromatic hydrocarbon based solvents such as benzene, and toluene; aliphatic hydrocarbon based solvents such as pentane, hexane, heptane, and methylcyclohexane; halogen based solvents such as methylene chloride, 1,2-dichloroethane, and chlorobenzene; sulfoxide type solvents such as dimethyl sulfoxide; amide type solvents such as N,N-dimethylformamide, and N,N-dimethylacetamide; urea based solvents such as dimethylpropyleneurea; phosphonic triamide type solvents such as hexamethylphosphonic triamide; ketone type solvents such as acetone, and methyl ethyl ketone; and nitrile type solvents such as acetonitrile, and propionitrile. These may be used alone, or two or more of them may be used in combination. When two or more of them are used in combination, the mixing ratio is not particularly limited. The amount of the reaction solvent is preferably no more than 50 times by weight, and more preferably no more than 20 times by weight based on the weight of the compound (5), because of disadvantages in terms of cost and post processing when too much solvent is used.

The pressure in the second reaction of the present invention may be less than 30 barr which can be generally practiced industrially, and more preferably less than 20 barr. The lower limit of the pressure is not particularly limited, and is preferably ambient pressure or higher.

The temperature in the present reaction may be predetermined ad libitum depending on the concentration of the solution of the ammonia, methylamine, ethylamine, or dimethylamine used, as well as the upper limit pressure of the reaction equipment. The temperature is preferably less than 110° C., and more preferably 40 to 90° C. The reaction time may be also predetermined ad libitum depending on the equivalence of the ammonia, methylamine, ethylamine, or dimethylamine used, as well as the upper limit pressure and the reaction temperature, and is preferably 1 to 24 hrs, and more preferably 3 to 12 hrs.

The order of addition of the reagents in the present reaction is not particularly limited, but may be arbitrarily determined.

According to the present reaction, the compound (6) can be produced while inhibiting racemization in the state in which the optical purity of the compound (5) is maintained. Thus, since the racemization is inhibited, and the optical purity is hardly reduced, the compound (6) having an optical purity of no less than 80% e.e., preferably no less than 90% e.e., and more preferably no less than 95% e.e., in general, can be produced depending on the optical purity of the compound (5).

As the post processing following the aminating reaction, any of general treatments for obtaining the product from the reaction mixture may be carried out. For example, the ammonia, methylamine, ethylamine, or dimethylamine may be removed by distillation from the reaction mixture after completing the reaction by an operation such as heating under reduced pressure; and an extraction operation may be conducted after adding an aqueous alkali solution such as an aqueous sodium hydroxide solution or an aqueous sodium bicarbonate solution to the residue as needed, and then adding a general extraction solvent, such as e.g., ethyl acetate, diethyl ether, toluene, hexane, methylene chloride or the like. The compound (6) can be obtained by removing the reaction solvent and the extraction solvent by distillation from the extraction liquid through an operation such as heating under reduced pressure. The compound (6) obtained in such a manner may include at least one from among the compound (5), an enantiomer of the compound (6), and a compound represented by the following formula (9);

[chemical formula 13]

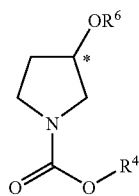

(9)

(wherein, * and $R^4$ are as defined above. $R^6$ represents a methyl group, an ethyl group, a n-propyl group, or an isopropyl group), or a compound represented by the following formula (10);

[chemical formula 14]

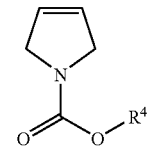

(10)

(wherein, $R^4$ is as defined above), as impurities. Next, since the yield achieved in the following step, or the purity of the compound obtained in the following step may be reduced when such compounds are used in the following step, process for removing these impurities are explained below.

More specifically, by forming a salt from the compound (6) and an acid, and then crystallizing with an organic solvent, the salt can be obtained as a crystal while the contaminated impurities are left in the mother liquid.

Herein, examples of the acid include e.g., inorganic acids such as hydrogen fluoride, hydrogen chloride, hydrogen bromide, hydrogen iodide, sulfuric acid, nitric acid, phosphoric acid, and boric acid; carboxylic acids such as formic acid, acetic acid, propionic acid, butyric acid, pivalic acid, chloroacetic acid, trichloroacetic acid, trifluoroacetic acid, oxalic acid, and mandelic acid; and sulfonic acids such as methanesulfonic acid, trifluoromethanesulfonic acid, benzenesulfonic acid, p-toluenesulfonic acid, and camphorsulfonic acid. The acid may be preferably hydrogen chloride, hydrogen bromide, sulfuric acid, acetic acid, pivalic acid, oxalic acid, mandelic acid, methanesulfonic acid, p-toluenesulfonic acid, or camphorsulfonic acid, more preferably hydrogen chloride, hydrogen bromide, acetic acid, methanesulfonic acid, or p-toluenesulfonic acid, and particularly preferably acetic acid. The amount of the acid used is preferably 0.5 to 5 times by mole, and more preferably 0.5 to 1.5 times by mole based on the mole of the compound (6).

Examples of the organic solvent which can be used include e.g., alcoholic solvents such as methanol, ethanol, n-propanol, isopropanol, n-butanol, tert-butanol, and ethylene glycol; ester type solvents such as ethyl acetate, n-propyl acetate, and isopropyl acetate; ether type solvents such as tetrahydrofuran, diethyl ether, 1,4-dioxane, methyl tert-butyl ether, and ethylene glycol dimethyl ether; ketone type solvents such as acetone, and methyl ethyl ketone; nitrile type solvents such as acetonitrile, and propionitrile; aromatic hydrocarbon based solvents such as benzene, and toluene; aliphatic hydrocarbon based solvents such as pentane, hexane, heptane, and methylcyclohexane; halogen based solvents such as methylene chloride, 1,2-dichloroethane, and chlorobenzene; sulfoxide type solvents such as dimethyl sulfoxide; amide type solvents such as N,N-dimethylformamide, and N,N-dimethylacetamide; urea based solvents such as dimethyl propyleneurea; and phosphonic triamide type solvents such as hexamethylphosphonic triamide. The organic solvent may be preferably methanol, ethanol, isopropanol, ethyl acetate, n-propyl acetate, isopropyl acetate, tetrahydrofuran, methyl tert-butyl ether, acetone, acetonitrile, toluene, hexane, heptane, or methylcyclohexane, and more preferably ethyl acetate, n-propyl acetate, isopropyl acetate, or toluene. These may be used alone, or two or more of them may be used in combination. When two or more of them are used in combination, the mixing ratio is not particularly limited. The amount of the organic solvent is preferably no more than 50 times by weight, and more preferably no more than 20 times by weight based on the weight of the compound (6), because of disadvantages in terms of cost and post processing when too much solvent is used.

Although the process for the crystallization with the organic solvent in this step is not particularly limited, for example, the following process may be exemplified.

(a) A process for crystallization by mixing the compound (6) with an aqueous solution of the acid or the acid and water in an organic solvent, and thereafter concentrating the mixture and removing the moisture by distillation. In this instance, an organic solvent azeotropic with water (for example, ethyl acetate, toluene or the like) may be used, whereby the azeotropic effect can be utilized in removing the moisture by distillation.

(b) A process for crystallization by mixing the compound (6) with the acid in an organic solvent.

(c) A process for crystallization by mixing the compound (6) with the acid in an organic solvent, and thereafter cooling.

The process for crystallization described above may be appropriately selected depending of the type of the acid, and the combination with the organic solvent. For example, in the case of hydrogen chloride or hydrogen bromide, since hydrochloric acid or hydrobromic acid, i.e., the aqueous solution thereof, can be more easily handled, the process (a) may be suited. To the contrary, in the case of use of an acid such as methanesulfonic acid or acetic acid which can be easily used generally as a nonhydrate, the process (b) is preferably selected. Alternatively, the salt obtained in the process (a), (b) or (c) may be used in combination with any of the crystallization processes of the following (d) to (f), or the salt obtained in the process (a), (b) or (c) may be dissolved in an organic solvent and may further subjected to any of the crystallization processes of (d) to (f). As a matter of course, the processes for crystallization (d) to (f) may be repeated ad libitum.

(d) A process of crystallization in which a salt of the compound (6) dissolved in an organic solvent is cooled.

(e) A process of crystallization in which a poor solvent is added to, or a poor solvent is used for enrichment and substitution of, the organic solvent including the salt of the compound (6) dissolved therein.

(f) A process of crystallization in which the salt of the compound (6) is dissolved in an organic solvent, and thereafter other acid is added.

As described above, the process (a), (b), (c), (d), (e) or (f) may be used in combination appropriately to permit crystallization.

As the organic solvent used in the process of crystallization, those similar to the organic solvents described above may be exemplified, and examples of the poor solvent which may be used in the process (e) include e.g., toluene, hexane, and the like. Moreover, a seed crystal may be added in crystallization.

The temperature in carrying out the processes of crystallization (a) to (f) is not particularly limited, and may be selected ad libitum depending on the type of the salt and the type of the solvent employed. Preferably, the temperature may be preset depending on the amount of the intended precipitate and the quality of the crystal within the range below the temperature at which the salt of the compound (6) is dissolved in the solvent or mixed solvent of the employed type.

The salt of the compound (6) precipitated in the processes of crystallization (a) to (f) can be separated and obtained by the procedure such as vacuum filtration, compression filtration, or centrifugation. In addition, when the purity of the crystal is deteriorated due to the remaining mother liquid in thus obtained crystal, the quality can be improved by further washing with an organic solvent as needed.

The drying of the crystal may be desirably carried out by a procedure of drying under reduced pressure (vacuum drying) at about no higher than 60° C., so as to avoid thermal decomposition and melting.

Since the aforementioned impurities can be removed by carrying out the process of crystallization, the chemical purity of the salt of the compound (6) is improved, and improvement of the optical purity is also enabled.

The salt of the compound (6) obtained by the aforementioned method can be further subjected to a treatment with a base such as an alkali metal hydroxide to release the compound (6), followed by operation such as extraction, concentration and the like, whereby the compound (6) having improved chemical purity can be also obtained.

EXAMPLES

Hereinafter, the present invention is explained in more detail by way of Examples, however, the present invention is not limited thereto. The chemical purity and the optical purity of the pyrrolidine derivatives demonstrated in Comparative Production Example 1 and subsequent description were analyzed by the following HPLC method.

Chemical Purity Analysis Method column: manufactured by Nacalai Tesque, Inc., {COSMOSIL® 5C18ARII 250×4.6 mm}, mobile phase: $KH_2PO_4$ buffer (pH 4.6)/acetonitrile=60/40 (v/v), flow rate: 1.0 ml/min, detection: UV 210 nm, column temperature: 40° C., retention time: acetic acid; 2.4 min, 1-(t-butoxycarbonyl)-3-aminopyrrolidine; 2.7 min, 1-benzyl-3-(methanesulfonyloxy)pyrrolidine; 3.9 min, 1-(tert-butoxycarbonyl)-3-(methanesulfonyloxy)pyrrolidine; 8.2 min Optical Purity Analysis Method:
1-(tert-butoxycarbonyl)-3-aminopyrrolidine column: manufactured by Daicel Chemical Industries, Ltd., {CROWNPAK 150×4.6 mm}, mobile phase: aqueous perchloric acid solution (pH 1.5), flow rate: 1.0 ml/min, detection: UV 210 nm, column temperature: 35° C., retention time: (S)-1-(tert-butoxycarbonyl)-3-aminopyrrolidine; 24.1 min, (R)-1-(tert-butoxycarbonyl)-3-aminopyrrolidine; 27.0 min Optical Purity Analysis Method:
1-(tert-butoxycarbonyl)-3-(methylamino)pyrrolidine In this method, measurement is carried out after Boc protection of the methylamino group at position 3 of 1-(tert-butoxycarbonyl)-3-(methylamino)pyrrolidine.

column: manufactured by Daicel Chemical Industries, Ltd., {CHIRALCEL OD-H 250×4.6 mm}, mobile phase: hexane/isopropyl alcohol=97.5/2.5 (v/v), flow rate: 1.0 ml/min, detection: UV 210 nm, column temperature: 30° C., retention time: Boc protected (R)-1-(tert-butoxycarbonyl)-3-methylaminopyrrolidine; 6.0 min, Boc protected (S)-1-(tert-butoxycarbonyl)-3-methylaminopyrrolidine; 6.9 min First Aspect of the Present Invention Comparative Example 1

Production of (R)-1-benzyl-3-aminopyrrolidine

An autoclave was cooled with an acetone/dry ice bath, and an ammonia gas was blown to pool 477 cc of liquid ammonia (corresponding to 25 equivalent of (S)-1-benzyl-3-(methane-sulfonyloxy)pyrrolidine). Thereto was added 180 g of (S)-1-benzyl-3-(methanesulfonyloxy)pyrrolidine (672.1 mmol, optical purity: 100% e.e.), which was heated to 100° C. whereby an internal pressure of 55 barr was observed. After allowing the reaction for 5 hrs, the reaction mixture was cooled to room temperature, and ammonia was removed by distillation under reduced pressure. As the residue, 306.7 g of a brown oily material was obtained (reaction yield: 88%, optical purity: 91.2% e.e.).

Comparative Example 2

Production of (R)-1-benzyl-3-aminopyrrolidine

An autoclave was cooled with an acetone/dry ice bath, and an ammonia gas was blown to pool 64 cc of liquid ammonia (corresponding to 25 equivalent of (S)-1-benzyl-3-(methane-sulfonyloxy)pyrrolidine). Thereto were added 30 g of (S)-1-benzyl-3-(methanesulfonyloxy)pyrrolidine (108.4 mmol, optical purity: 100% e.e.) and 118 g of methanol, which was heated to 100° C. whereby an internal pressure of 10 barr was observed. After allowing the reaction for 7 hrs, the reaction mixture was cooled to room temperature, and ammonia and methanol were removed by distillation under reduced pressure. As the residue, 26.6 g of a pale yellow oily material was obtained (reaction yield: 67%, optical purity: 85.8% e.e.).

Example 1

Step 1-1: Production of
(R)-1-benzyl-3-aminopyrrolidine

In an autoclave were charged 5.303 g of (S)-1-benzyl-3-(methanesulfonyloxy)pyrrolidine (20 mmol, optical purity: 100% e.e.), and 42.53 g of 40% by weight aqueous ammonia (50 equivalent), which was heated to 80° C. whereby an internal pressure of 8 barr was observed. After allowing the reaction for 20 hrs, the reaction mixture was cooled to room temperature, followed by addition of 4.00 g of a 30% by weight aqueous sodium hydroxide solution (1.5 equivalent), and then ammonia was removed by distillation under reduced pressure. The residue was extracted with 30 mL of ethyl acetate three times, and the organic layers were combined. After washing with 3 mL of a saturated brine, drying over anhydrous magnesium sulfate, and concentration under reduced pressure gave 3.6146 g of a dark red oily material (reaction yield: 73%, optical purity: 92.4% e.e.).

Results of Example 5, Comparative Example 1, Comparative Example 2, and Example 1 of Japanese Patent No. 3639449 are summarized in Table below.

According to Example 5 of Japanese Patent No. 3639449, (R)-1-benzyl-3-aminopyrrolidine of 96.8% e.e. was obtained under a condition which can be hardly practiced industrially, i.e., at a reaction temperature of 110° C., under a pressure of 80 barr. However, when the reaction temperature and the reaction pressure were lowered with reference to Example 5 of Japanese Patent No. 3639449 described above, the reaction proceeded favorably, but the optical purity was lowered to 91.2% e.e. (Comparative Example 1). When the reaction was allowed at a reaction temperature of 100° C., under a pressure of 10 barr, with addition of methanol in place of water used in the present invention, the product exhibited an optical purity of 85.8% e.e. (Comparative Example 2). When the reaction was allowed under a pressure of equal to or less than of 30 barr which can be practiced industrially, i.e., 8 barr at 80° C., after adding water, the product exhibited an optical purity of 92.4% e.e. (Example 1), showing the results almost the same as those by the reaction in liquid ammonia under a pressure of 55 barr.

TABLE 1

|  | Reaction temperature (° C.) | Reaction pressure (barr) | Reaction time (hour) | Reaction yield (%) | Optical purity (% e.e.) |
| --- | --- | --- | --- | --- | --- |
| Example 5 of Japanese Patent No. 3639449 | 110 | 80 | 2.5 | 93 | 96.8 |
| Comparative Example 1 | 100 | 55 | 5 | 88 | 91.2 |
| Comparative Example 2 | 100 | 10 | 7 | 67 | 85.8 |
| Example 1 | 80 | 8 | 20 | 73 | 92.4 |

Step 1-2: Production of
(R)-1-benzyl-3-aminopyrrolidine Acetic Acid Salt

When 960 mg of acetic acid (16 mmol) was added to a solution in ethyl acetate (30 mL) of 3.6146 g of crude (R)-1-benzyl-3-aminopyrrolidine produced in the step 1-1 (14.6 mmol, optical purity: 92.4% e.e., including 29.5% by weight 1-benzyl-3-pyrrolidinol, and 0.8% by weight 1-benzyl-2,5-dihydro-1H-pyrrole as impurities), a crystal was precipitated. After stirring at 5° C. for 30 min, the crystal was filtrated under reduced pressure, which was washed with 20 mL of ethyl acetate, and thereafter vacuum drying was carried out to give a white crystal of 2.5804 g (yield: 75%, optical purity: 94.3% e.e., with no 1-benzyl-3-pyrrolidinol and 1-benzyl-2,5-dihydro-1H-pyrrole detected).

Step 1-3: Production of
(R)-1-benzyl-3-aminopyrrolidine Hydrobromic Acid
Salt

To a solution in isopropanol (20 mL) of 1.00 g of (R)-1-benzyl-3-aminopyrrolidine acetic acid salt (4.23 mmol) produced in the step 1-2 was added 714 mg of 48% by weight hydrobromic acid (1 equivalent), and concentrated under reduced pressure. To the residue was added 20 mL of isopropanol, and concentrated again. When 1 mL of isopropanol and 20 mL of ethyl acetate were added to the residue, a crystal was precipitated. After stirring at 20° C. for 30 min, the crystal was filtrated under reduced pressure, which was washed with 10 mL of ethyl acetate, and thereafter vacuum drying was carried out to give a white crystal of 700.9 mg (yield: 64%, optical purity: 98.7% e.e.).

Example 2

Production of
(R)-1-(tert-butoxycarbonyl)-3-aminopyrrolidine
Acetic Acid Salt

In an autoclave were charged 11.2 g of (S)-1-(tert-butoxycarbonyl)-3-(methanesulfonyloxy)pyrrolidine (29.5 mmol), and 62.7 g of 40% by weight aqueous ammonia (50 equivalent), which was heated to 80° C. whereby an internal pressure of 8 barr was observed. After allowing the reaction for 10 hrs, the reaction mixture was cooled to room temperature, followed by concentration under reduced pressure. To the residue were added 4.13 g of a 30% by weight aqueous sodium hydroxide solution, 31.3 g of a saturated brine, and 19.6 g of toluene to execute extraction. By concentrating under reduced pressure, 5.09 g of a yellow oily material was obtained. When 53.8 g of toluene, and 1.43 g of acetic acid (0.8 equivalent) were added sequentially thereto, a crystal was precipitated. After stirring at 20° C. for 13 hrs, the crystal was filtrated under reduced pressure, which was washed with 16.2 mL of toluene, and thereafter vacuum drying was carried out to give a white crystal of 4.81 g (yield: 67%, purity: 100% by weight, optical purity: 99.9% e.e.)

$^1$H-NMR (CDCl$_3$, 400 MHz): δ (ppm) 1.45 (s, 9H), 1.88 (m, 1H), 1.97 (s, 3H), 2.13 (m, 1H), 3.16-3.32 (m, 1H), 3.40 (m, 1H), 3.46-3.62 (m, 2H), 3.66 (m, 1H), 6.63 (m, 2H)

Example 3

Production of (R)-1-(benzyloxycarbonyl)-3-aminopyrrolidine Acetic Acid Salt

In an autoclave were charged 2.44 g of (S)-1-(benzyloxycarbonyl)-3-(methanesulfonyloxy)pyrrolidine (7.38 mmol), and 15.7 g of 40% by weight aqueous ammonia (50 equivalent), which was heated to 80° C. whereby an internal pressure of 8 barr was observed. After allowing the reaction for 16 hrs, the reaction mixture was cooled to room temperature, followed by addition of a 30% by weight aqueous sodium hydroxide solution to adjust the pH to 13, and then ammonia was removed by distillation under reduced pressure. The residue was extracted with 15 mL of ethyl acetate three times, and the organic layers were combined. After washing with 3 mL of a saturated brine, drying over anhydrous magnesium sulfate, and concentration under reduced pressure gave a yellow oily material. When 10 mL of ethyl acetate, and 354 mg of acetic acid (0.8 equivalent) were added sequentially thereto, a crystal was precipitated. After stirring at 5° C. for 30 min, the crystal was filtrated under reduced pressure, which was washed with 10 mL of ethyl acetate, and thereafter vacuum drying was carried out to give a white crystal of 1.1684 g (yield: 56%, purity: 100% by weight, optical purity: 100% e.e.)

$^1$H-NMR (D$_2$O, 400 MHz): δ (ppm) 1.75 (s, 3H), 1.95 (m, 1H) 2.20 (m, 1H), 3.3-3.4 (m, 3H), 3.57 (m, 1H), 3.83 (m, 1H), 5.00 (s, 2H), 7.29 (m, 5H)

Example 4

Production of (R)-1-benzyl-3-(methylamino)pyrrolidine Hydrobromic Acid Salt

In an autoclave were charged 5.303 g of (S)-1-benzyl-3-(methanesulfonyloxy)pyrrolidine (20 mmol), and 51.9 mL of a 40% by weight aqueous methylamine solution (30 equivalent), which was heated to 80° C. whereby an internal pressure of 2 barr was observed. After allowing the reaction for 16 hrs, the reaction mixture was cooled to room temperature, followed by concentration under reduced pressure. To the residue was added 4.00 g of a 30% by weight aqueous sodium hydroxide solution, and extracted with 30 mL of ethyl acetate three times. The organic layers were combined, washed with 5 mL of a saturated brine, and concentrated under reduced pressure to give 4.20 g of a yellow oily material. Thereto were added 35 mL of isopropanol, and 3.04 g of 48% by weight hydrobromic acid (0.93 equivalent), followed by concentration under reduced pressure. When 35 mL of ethyl acetate was added to the residue, a crystal was precipitated. After stirring at 5° C. for 30 min, the crystal was filtrated under reduced pressure, which was washed with 18 mL of cooled ethyl acetate, and thereafter vacuum drying was carried out to give a white crystal of 4.65 g (yield: 86%, purity: 100% by weight, optical purity: 98.3% e.e.)

$^1$H-NMR (D$_2$O, 400 MHz): δ (ppm) 1.73 (m, 1H), 2.17 (m, 1H) 2.47 (s, 3H), 2.51 (m, 1H), 2.54 (m, 2H), 2.98 (m, 1H), 3.55 (m, 1H), 3.64 (s, 2H), 7.25 (s, 5H)

Reference Example 1

Production of (S)-1-benzyl-3-(methanesulfonyloxy)pyrrolidine (S)-1-benzyl-3-hydroxypyrrolidine in an amount of 44.18 g was dissolved in 38.34 g of toluene, and thereto was added 66.88 g of a 30% by weight aqueous sodium hydroxide solution. Next, methanesulfonyl chloride was added dropwise at a rate to allow the internal temperature to be kept at 5 to 10° C. After sodium chloride which was precipitated in the aqueous layer was dissolved by adding 90 ml of water, and liquid separation was performed, thus obtained organic layer was concentrated under reduced pressure to give the title compound as 60.14 g of a pale brown oily material.

$^1$H-NMR (CDCl$_3$): δ (ppm) 2.08 (m, 1H), 2.28 (m, 1H), 2.49 (m, 1H), 2.99 (s, 3H), 3.65 (m, 2H), 7.30-7.33 (m, 5H)

Comparative Production Example 1

Production of (S)-1-(tert-butoxycarbonyl)-3-(methanesulfonyloxy)pyrrolidine (S)-1-benzyl-3-(methanesulfonyloxy)pyrrolidine produced by the method described in Reference Example 1, in an amount of 1.39 g, was dissolved in 10 ml of methanol, and thereto were added 678 mg of conc. hydrochloric acid, and 128 mg of 5% by weight palladium-carbon. Then the mixture was stirred in a hydrogen atmosphere under an ordinary pressure at 40° C., for 18 hrs. After palladium was filtrated under reduced pressure, washing obtained using 10 ml of methanol was included. Thus obtained filtrate was concentrated under reduced pressure to obtain a concentrate. Thereto were added 10 ml of water and 10 ml of ethyl acetate, and then added 660 mg of triethylamine, and 1.13 g of di tert-butyl dicarbonate under cooling on ice, followed by stirring for 30 min. After conducting liquid separation, the organic layer was washed with 10 ml of water, and the resulting organic layer was concentrated under reduced pressure to give 1.23 g of the title compound as a colorless and transparent oily material (chemical purity: 97.6 area %, yield: 86%).

$^1$H-NMR (CDCl$_3$): δ (ppm) 1.47 (s, 9H), 2.15 (m, 1H), 2.27 (m, 1H), 3.05 (s, 3H), 3.42-3.78 (m, 4H), 5.26 (m, 1H)

Production Example 1

Production of (S)-1-(tert-butoxycarbonyl)-3-(methanesulfonyloxy)pyrrolidine (S)-1-benzyl-3-(methanesulfonyloxy)pyrrolidine produced by the method described in Reference Example 1, in an amount of 1.39 g, was dissolved in 10 ml of methanol, and thereto were added 1.13 g of di t-butyl dicarbonate and 127 mg of 5% by weight palladium-carbon. Then the mixture was stirred in a hydrogen atmosphere under an ordinary pressure at 24° C. for 3 hrs. After palladium was filtrated under reduced pressure, washing obtained using 30 ml of methanol was included. Thus obtained filtrate was concentrated under reduced pressure to give 1.37 g of the title compound as a pale yellow oily material (chemical purity: 90.9 area %, yield:

96%). The title compound could be obtained at an extremely high yield as compared with the case of Comparative Production Example 1.

Production Example 2

Production of (S)-1-(tert-butoxycarbonyl)-3-(methanesulfonyloxy)pyrrolidine

To 627 g of a solution in toluene of 180 g of (S)-1-benzyl-3-(methanesulfonyloxy)pyrrolidine produced by the method described in Reference Example 1 were added 159 g of di t-butyl dicarbonate and 27 g of 10% palladium carbon. Then the mixture was stirred in a hydrogen atmosphere under an ordinary pressure at 22° C. for 7 hrs. After palladium was filtrated under reduced pressure, washing obtained using 270 g of toluene was included. Thus obtained filtrate was concentrated under reduced pressure to give 238 g of a solution in toluene of 167 g of the title compound (yield: 89%, chemical purity: 93.0 area %, optical purity: 100% e.e.).

Example 5

Step 5-1: Production of
(R)-1-(tert-butoxycarbonyl)-3-aminopyrrolidine

To 5.56 g of (S)-1-(tert-butoxycarbonyl)-3-(methanesulfonyloxy)pyrrolidine produced by the method described in Production Example 2 was added 36.4 g of a 28% by weight aqueous ammonia solution, and the mixture was stirred at 90° C. for 19 hrs (internal pressure: about 4 barr). After cooling, ammonia was removed by distillation, and thereto were added 10 ml of water and 3.21 g of a 30% by weight aqueous sodium hydroxide solution. After the aqueous solution was concentrated under reduced pressure, 10 ml of a saturated brine was added thereto, and the target substance was extracted with 20 ml of ethyl acetate three times. Thus obtained organic layer was washed with 3 ml of a saturated brine, followed by concentration under reduced pressure to give the title compound as 3.20 g of a yellow liquid (chemical purity: 63.5 area %, optical purity: 100% e.e., yield: 64%). It was ascertained that 41.4% of the optically active 1-(tert-butoxycarbonyl)-3-hydroxypyrrolidine represented by the above formula (3) was contaminated with respect to the HPLC area value of the title compound, while 7.8% of 1-(tert-butoxycarbonyl)-3,4-dehydropyrrolidine represented by the above formula (4) was contaminated with respect to the HPLC area value of the title compound.

Step 5-2: Production of
(R)-1-(tert-butoxycarbonyl)-3-aminopyrrolidine
Acetic Acid Salt (R)-1-(tert-butoxycarbonyl)-3-aminopyrrolidine obtained in the step 5-1 (chemical purity: 63.5 area %, contaminated with 41.4% of the optically active 1-(tert-butoxycarbonyl)-3-hydroxypyrrolidine represented by the above formula (3) with respect to the HPLC area value of the title compound, and with 7.8% of 1-(tert-butoxycarbonyl)-3,4-dehydropyrrolidine represented by the above formula (4) with respect to the HPLC area value of the title compound) in an amount of 3.20 g was dissolved in 42.2 g of ethyl acetate, to which 990 mg of acetic acid was added. After stirring for 30 min under cooling on ice, 2.53 g of hexane was added thereto, followed by additional stirring for 30 min. The crystal was filtrated under reduced pressure. After the crystal was washed with 5.06 g of a solution consisting of ethyl acetate and hexane, vacuum drying was carried out to give the title compound as 2.78 g of a white solid (chemical purity: 99.8 area %, yield: 88%, no enantiomer detected). It was ascertained that the optically active 1-(tert-butoxycarbonyl)-3-hydroxypyrrolidine represented by the above formula (3) decreased to 0.22% with respect to the HPLC area value of the title compound, while the 1-(tert-butoxycarbonyl)-3,4-dehydropyrrolidine represented by the above formula (4) was not detected on HPLC.

Example 6

Step 6-1: Production of
(R)-1-(tert-butoxycarbonyl)-3-aminopyrrolidine

To 11.2 g of a solution in toluene including 7.83 g of (S)-1-(tert-butoxycarbonyl)-3-(methanesulfonyloxy)pyrrolidine produced by the method described in Production Example 2 was added 62.7 g of a 40% by weight aqueous ammonia solution, and the mixture was stirred at 80° C. for 10 hrs (internal pressure: about 8 barr). After cooling, the reaction mixture was concentrated under reduced pressure, to which 31.3 g of a saturated brine, 19.6 g of toluene, and 4.13 g of a 30% by weight aqueous sodium hydroxide solution were added. Thus obtained organic layer was concentrated under reduced pressure to give the title compound as 5.09 g of a yellow liquid (chemical purity: 74.5 area %, yield: 74%, optical purity: 99.4% ee). It was ascertained that 18.1% of the optically active 1-(tert-butoxycarbonyl)-3-hydroxypyrrolidine represented by the above formula (3) was contaminated with respect to the HPLC area value of the title compound, while 4.1% of 1-(tert-butoxycarbonyl)-3,4-dehydropyrrolidine represented by the above formula (4) was contaminated with respect to the HPLC area value of the title compound.

Step 6-2: Production of
(R)-1-(tert-butoxycarbonyl)-3-aminopyrrolidine
Acetic Acid Salt (R)-1-(tert-butoxycarbonyl)-3-aminopyrrolidine obtained in the step 6-1 (chemical purity: 74.5 area %, optical purity: 99.4% ee, contaminated with 18.1% of the optically active 1-(tert-butoxycarbonyl)-3-hydroxypyrrolidine represented by the above formula (3) with respect to the HPLC area value of the title compound, and with 4.1% of 1-(tert-butoxycarbonyl)-3,4-dehydropyrrolidine represented by the above formula (4) with respect to the HPLC area value of the title compound) in an amount of 5.09 g was dissolved in 58.3 g of toluene, to which 1.43 g of acetic acid was added. After stirring at 22° C. for 13 hrs, the crystal was filtrated under reduced pressure. After the crystal was washed with 16 ml of toluene, vacuum drying was carried out to give the title compound as 4.81 g of a white solid (chemical purity: 99.6 area %, yield: 90%, optical purity: 99.9% ee). It was ascertained that the optically active 1-(tert-butoxycarbonyl)-3-hydroxypyrrolidine represented by the above formula (3) decreased to 0.30% with respect to the HPLC area value of the title compound, while the 1-(tert-butoxycarbonyl)-3,4-dehydropyrrolidine represented by the above formula (4) was not detected on HPLC.

Step 6-3: Production of
(R)-1-(tert-butoxycarbonyl)-3-aminopyrrolidine

To 611 mg of (R)-1-(tert-butoxycarbonyl)-3-aminopyrrolidine acetic acid salt (chemical purity: 99.8 area %) obtained by producing with the process described in the step 6-2 were added 1.22 g of a 23% by weight brine, 2.45 g of toluene, and 367 mg of a 30% by weight aqueous sodium hydroxide solution, and the mixture was stirred. After conducting liquid separation, the organic layer was concentrated. Then vacuum drying was carried out to give the title compound as 480 mg of a colorless and transparent liquid (chemical purity: 99.6 area %).

Example 7

Step 7-1: Production of (S)-1-(tert-butoxycarbonyl)-3-methylaminopyrrolidine Hydrochloric Acid Salt To 7.58 g of a solution in toluene including 5.31 g of (R)-1-(tert-butoxycarbonyl)-3-(methanesulfonyloxy)pyrrolidine produced by the method described in Production Example 2 was added 77.7 g of a 40% by weight aqueous methylamine solution, and the mixture was stirred at 80° C. for 18 hrs (internal pressure: about 2 barr). After cooling, the reaction mixture was concentrated under reduced pressure, to which 21.2 g of a saturated brine, 13.3 g of toluene, and 2.81 g of a 30% by weight aqueous sodium hydroxide solution were added. Thus obtained organic layer was concentrated under reduced pressure to give the title compound as 4.61 g of a yellow liquid. Thereto were added 40 mL of isopropanol, and 1.72 g of conc. hydrochloric acid (0.83 equivalent), and then the mixture was concentrated under reduced pressure. When 53.9 g of ethyl acetate was added to the residue, a crystal was precipitated. After the mixture was stirred at 22° C. for 1 hour, and further stirred at 4° C. for 1 hour, the crystal was filtrated under reduced pressure. The crystal was washed with 15 mL of cooled ethyl acetate, and thereafter vacuum drying was carried out to give the title compound as 3.45 g of a white solid (chemical purity: 100.0 area %, yield: 73%, optical purity: 99.5% ee). The optically active 1-(tert-butoxycarbonyl)-3-hydroxypyrrolidine represented by the above formula (3) decreased to 0.03% with respect to the HPLC area value of the title compound (6.4% before the crystallization). It was ascertained that the 1-(tert-butoxycarbonyl)-3,4-dehydropyrrolidine represented by the above formula (4) was not detected on HPLC (1.6% before the crystallization).

$^1$H-NMR (CDCl$_3$): δ (ppm) 1.47 (s, 9H), 2.36 (m, 2H), 2.72 (s, 3H), 3.39 (m, 1H), 3.60-3.70 (m, 3H), 3.81 (m, 1H), 9.91 (m, 1H)

Step 7-2: Production of (R)-1-(tert-butoxycarbonyl)-3-methylaminopyrrolidine

To 1.18 g of (R)-1-(tert-butoxycarbonyl)-3-methylaminopyrrolidine hydrochloric acid salt (chemical purity: 99.9 area %) obtained by producing with the process described in the step 7-1 were added 2.30 g of a 23% by weight brine, 4.71 g of toluene and 734 mg of a 30% by weight aqueous sodium hydroxide solution, and the mixture was stirred. After conducting liquid separation, the organic layer was concentrated. Then vacuum drying was carried out to give the title compound as 946 mg of a colorless and transparent liquid (chemical purity: 99.3 area %, yield 97%).

$^1$H-NMR (CDCl$_3$): δ (ppm) 1.45 (s, 9H), 1.71 (m, 2H), 2.04 (m, 1H), 2.44 (s, 3H), 3.03-3.28 (m, 2H), 3.29-3.65 (m, 3H)

Example 8

Step 8-1: Production of (R)-1-(tert-butoxycarbonyl)-3-ethylaminopyrrolidine Hydrochloric Acid Salt To 7.58 g of a solution in toluene including 5.31 g of (S)-1-(tert-butoxycarbonyl)-3-(methanesulfonyloxy)pyrrolidine produced by the method described in Production Example 2 was added 64.4 g of a 70% by weight aqueous ethylamine solution, and the mixture was stirred at 80° C. for 18 hrs (internal pressure: about 2 barr). After cooling, the reaction mixture was concentrated under reduced pressure, to which 21.2 g of a saturated brine, 13.3 g of toluene, and 2.80 g of a 30% by weight aqueous sodium hydroxide solution were added. Thus obtained organic layer was concentrated under reduced pressure to give the title compound as 5.61 g of a yellow liquid. Thereto were added 40 mL of isopropanol, and 1.89 g of conc. hydrochloric acid (0.91 equivalent), and then the mixture was concentrated under reduced pressure. When 53.9 g of ethyl acetate was added to the residue, a crystal was precipitated. After the mixture was stirred at 22° C. for 1 hour, and further stirred at 4° C. for 1 hour, the crystal was filtrated under reduced pressure. The crystal was washed with 15 mL of cooled ethyl acetate, and thereafter vacuum drying was carried out to give the title compound as 3.91 g of a white solid (chemical purity: 99.7 area %, yield: 78%). The optically active 1-(tert-butoxycarbonyl)-3-hydroxypyrrolidine represented by the above formula (3) decreased to 0.03% with respect to the HPLC area value of the title compound (6.1% before the crystallization). The 1-(tert-butoxycarbonyl)-3,4-dehydropyrrolidine represented by the above formula (4) was decreased to 0.02% with respect to the HPLC area value of the title compound (20.1% before the crystallization).

$^1$H-NMR (CDCl$_3$): δ (ppm) 1.45 (s, 9H), 1.53 (t, 3H), 2.27-2.49 (m, 2H), 3.07 (m, 2H), 3.35 (m, 1H), 3.66 (m, 3H), 3.86 (m, 1H), 9.97 (m, 1H)

Step 8-2: Production of (R)-1-(tert-butoxycarbonyl)-3-ethylaminopyrrolidine

To 1.25 g of (R)-1-(tert-butoxycarbonyl)-3-ethylaminopyrrolidine hydrochloric acid salt (chemical purity: 99.7 area %) obtained in the step 8-1 were added 2.46 g of a 23% by weight brine, 5.03 g of toluene and 733 mg of a 30% by weight aqueous sodium hydroxide solution, and the mixture was stirred. After conducting liquid separation, the organic layer was concentrated. Then vacuum drying was carried out to give the title compound as 1.05 g of a colorless and transparent liquid (chemical purity: 99.2 area %, yield 98%).

$^1$H-NMR (CDCl$_3$): δ (ppm) 1.12 (t, 3H), 1.48 (s, 9H), 1.68 (m, 2H), 2.06 (m, 1H), 2.65 (m, 2H), 3.02-3.10 (m, 1H), 3.25-3.57 (m, 4H)

Example 9

Step 9-1: Production of (R)-1-(tert-butoxycarbonyl)-3-dimethylaminopyrrolidine Hydrochloric Acid Salt To 7.58 g of a solution in toluene including 5.31 g of (S)-1-(tert-butoxycarbonyl)-3-(methanesulfonyloxy)pyrrolidine produced by the method described in Production Example 2 was added 90.2 g of a 50% by weight aqueous dimethylamine solution, and the mixture was stirred at 80° C. for 18 hrs (internal pressure: about 2 barr). After cooling, the reaction mixture was concentrated under reduced pressure, to which 21.2 g of a saturated brine, 13.3 g of toluene, and 2.80 g of a 30% by weight aqueous sodium hydroxide solution were added. Thus obtained organic layer was concentrated under reduced pressure to give the title compound as 5.43 g of a yellow liquid. Thereto were added 40 mL of isopropanol, and 1.86 g of conc. hydrochloric acid (0.89 equivalent), and then the mixture was concentrated under reduced pressure. When 53.9 g of ethyl acetate was added to the residue, a crystal was precipitated. After the mixture was stirred at 22° C. for 1 hour, and further stirred at 4° C. for 1 hour, the crystal was filtrated under reduced pressure. The crystal was washed with 15 mL of cooled ethyl acetate, and thereafter vacuum drying was carried out to give the title compound as 3.83 g of a white solid (chemical purity: 99.9 area %, yield: 75%). The optically active 1-(tert-butoxycarbonyl)-3-hydroxypyrrolidine represented by the above formula (3) was ascertained to be undetected on HPLC (4.6% before the crystallization). Moreover, the 1-(tert-butoxycarbonyl)-3,4-dehydropyrrolidine represented by the above formula (4) was ascertained to be undetected on HPLC (3.9% before the crystallization).

$^1$H-NMR (CDCl$_3$): δ (ppm) 1.46 (s, 9H), 1.89 (m, 1H), 2.35 (m, 1H), 2.84 (s, 6H), 3.38 (m, 1H), 3.51-3.91 (m, 4H)

Step 9-2: Production of (R)-1-(tert-butoxycarbonyl)-3-dimethylaminopyrrolidine

To 1.25 g of (R)-1-(tert-butoxycarbonyl)-3-dimethylaminopyrrolidine hydrochloric acid salt (chemical purity: 99.9 area %) obtained in the step 9-1 were added 2.46 g of a 23% by weight brine, 5.03 g of toluene and 738 mg of a 30% by weight aqueous sodium hydroxide solution, and the mixture was stirred. After conducting liquid separation, the organic layer was concentrated. Then vacuum drying was carried out to give the title compound as 999 mg of a colorless and transparent liquid (chemical purity: 99.5 area %, yield 95%).

$^1$H-NMR (CDCl$_3$): δ (ppm) 1.46 (s, 9H), 1.74 (m, 1H), 2.05 (m, 1H), 2.24 (s, 6H), 2.63 (m, 1H), 3.05 (m, 1H), 3.27 (m, 1H), 3.45-3.69 (m, 2H)

Second Aspect of the Present Invention

Example 10

Step 10-1: Production of (R)-1-(tert-butoxycarbonyl)-3-aminopyrrolidine (S)-1-(tert-butoxycarbonyl)-3-(methanesulfonyloxy)pyrrolidine produced by the method described in Production Example 2 in an amount of 5.52 g was dissolved in 10 ml of methanol, and thereto was added 56 ml of an ammonia/methanol solution (10.7 mol/l) prepared beforehand. The mixture was stirred at 80° C. for 16 hrs (internal pressure: about 9 barr). After cooling, ammonia was removed by distillation, to which 10 ml of water, and 3.21 g of a 30% by weight aqueous sodium hydroxide solution were added. After the aqueous solution was concentrated under reduced pressure, 10 ml of a saturated brine 10 ml was added thereto, and the target substance was extracted with 20 ml of ethyl acetate three times. Thus obtained organic layer was washed with 3 ml of a saturated brine, followed by concentration under reduced pressure to give the title compound as 4.35 g of a yellow liquid (chemical purity: 48.0 area %, yield: 72%, optical purity: 96.6% ee). It was ascertained that 48.4% of the optically active 1-(tert-butoxycarbonyl)-3-methoxypyrrolidine represented by the above formula (9) was contaminated with respect to the HPLC area value of the title compound, while 31.5% of 1-(tert-butoxycarbonyl)-3,4-dehydropyrrolidine represented by the above formula (10) was contaminated with respect to the HPLC area value of the title compound.

$^1$H-NMR (CDCl$_3$): δ (ppm) 1.22 (m, 2H), 1.46 (s, 9H), 1.65 (m, 1H), 2.04 (m, 1H), 3.03 (m, 1H), 3.36-3.59 (m, 4H)

Step 10-2: Production of (R)-1-(tert-butoxycarbonyl)-3-aminopyrrolidine Acetic Acid Salt (R)-1-(tert-butoxycarbonyl)-3-aminopyrrolidine obtained in the step 10-1 (chemical purity: 48.0 area %, optical purity: 96.6% ee, contaminated with 48.4% of the optically active 1-(tert-butoxycarbonyl)-3-methoxypyrrolidine represented by the above formula (9) with respect to the HPLC area value of the title compound, and with 31.5% of 1-(tert-butoxycarbonyl)-3,4-dehydropyrrolidine represented by the above formula (10) with respect to the HPLC area value of the title compound) in an amount of 4.35 g was dissolved in 50 ml of ethyl acetate, to which 951 mg of acetic acid was added. After stirring for 30 min under cooling on ice, 2.69 g of hexane was added thereto, followed by additional stirring for 30 min. The crystal was filtrated under reduced pressure. After the crystal was washed with 20 ml of a solution consisting of ethyl acetate and hexane, vacuum drying was carried out to give the title compound as 2.80 g of a white solid (chemical purity: 100.0 area %, yield: 82%, optical purity: 99.0% ee). It was ascertained that the optically active 1-(tert-butoxycarbonyl)-3-methoxypyrrolidine represented by the above formula (9), and the 1-(tert-butoxycarbonyl)-3,4-dehydropyrrolidine represented by the above formula (10) were not detected on HPLC.

$^1$H-NMR (CDCl$_3$): δ (ppm) 1.45 (s, 9H), 1.88 (m, 1H), 1.97 (s, 3H), 2.13 (m, 1H), 3.16-3.32 (m, 1H), 3.40 (m, 1H), 3.46-3.62 (m, 2H), 3.66 (m, 1H), 6.63 (m, 2H)

Step 10-3: Production of (R)-1-(tert-butoxycarbonyl)-3-aminopyrrolidine Hydrochloric Acid Salt To 30 ml of a solution in isopropanol including 2.60 g of (R)-1-(tert-butoxycarbonyl)-3-aminopyrrolidine produced by the method described in the step 10-1 (chemical purity: 48.7 area %, optical purity: 96.6% ee, contaminated with 48.4% of the optically active 1-(tert-butoxycarbonyl)-3-methoxypyrrolidine represented by the above formula (9) with respect to the HPLC area value of the title compound, and with 31.9% of 1-(tert-butoxycarbonyl)-3,4-dehydropyrrolidine represented by the above formula (10) with respect to the HPLC area value of the title compound) was added 1.39 g of conc. hydrochloric acid, and concentrated under reduced pressure. Thereto was added 50 ml of ethyl acetate, and stirred at 22° C. for 30 min. After stirring for additional 30 min under cooling on ice, the crystal was filtrated under reduced pressure. The crystal was washed with 20 ml of ethyl acetate, and thereafter vacuum drying was carried out to give the title compound as 2.51 g of a white solid (chemical purity: 99.6 area %, yield: 95%, optical purity: 99.7% ee). It was ascertained that the optically active 1-(tert-butoxycarbonyl)-3-methoxypyrrolidine represented by the above formula (9), and the 1-(tert-butoxycarbonyl)-3,4-dehydropyrrolidine represented by the above formula (10) were not detected on HPLC.

The invention claimed is:

1. A process for the production of an optically active 3-amino nitrogen-containing compound represented by the following formula (2);

[chemical formula 15]

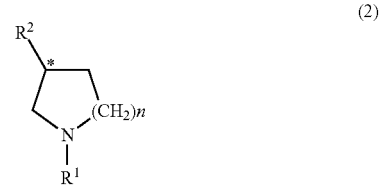

(2)

wherein, $R^1$ represents an alkyl group having 1 to 20 carbon atoms which may have a substituent, a cycloalkyl group having 3 to 20 carbon atoms which may have a substituent, an alkenyl group having 2 to 20 carbon atoms which may have a substituent, an aralkyl group having 7 to 20 carbon atoms which may have a substituent, an aryl group having 6 to 20 carbon atoms which may have a substituent, a heteroaryl group having 3 to 20 carbon atoms which may have a substituent, a hydroxyl group, an alkyloxy group having 1 to 20 carbon atoms, an aryloxy group having 6 to 20 carbon atoms, an aralkyloxy group having 7 to 20 carbon atoms, or a protecting group of an amino group; * represents an asymmetric carbon atom; n represents an integer of 1 to 3; and $R^2$ is an amino group, a methylamino group, an ethylamino group or a dimethylamino group, in which the position 3 is sterically inverted from the starting material, the process comprising allowing an optically active 3-substituted nitrogen-containing compound represented by the following formula (1);

[chemical formula 16]

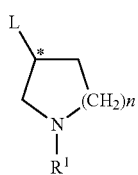

(1)

wherein, *, $R^1$ and n are as defined above; and L represents a leaving group, to react with ammonia, methylamine, ethylamine or dimethylamine in the presence of water, wherein the amount of water used is 0.1 to 10 times by weight on the weight of ammonia, methylamine, ethylamine, or dimethylamine, and wherein the reaction with ammonia, methylamine, ethylamine or dimethylamine is carried out at a temperature of less than 100° C., under a pressure of less than 10 barr.

2. The process for the production according to claim 1 wherein L is an alkylsulfonyloxy group having 1 to 20 carbon atoms which may have a substituent, an arylsulfonyloxy group having 6 to 20 carbon atoms which may have a substituent, or a chlorine atom.

3. The process for the production according to claim 1 wherein L is a methanesulfonyloxy group.

4. The process for the production according to claim 1 wherein $R^1$ is a benzyl group, an allyl group, a hydroxyl group, an acetyl group, a benzoyl group, a methoxycarbonyl group, an ethoxycarbonyl group, an isopropoxy carbonyl group, a tert-butoxycarbonyl group, or a benzyloxycarbonyl group.

5. The process for the production according to claim 1 wherein $R^1$ is a benzyl group, a tert-butoxycarbonyl group, or a benzyloxycarbonyl group.

6. The process for the production according to claim 1 wherein the compound (1) is an optically active 3-substituted pyrrolidine derivative in which n is an integer of 1, and the compound (2) is an optically active 3-aminopyrrolidine derivative in which n is an integer of 1.

7. A process for the production of a salt of an optically active 3-amino nitrogen-containing compound which comprises: forming a salt from an acid and the compound (2) produced by the process according to any one of claims 1 to 6; and crystallizing from an organic solvent, thereby obtaining the salt as a crystal while caving contaminated impurities in the mother liquid.

8. The process for the production according to claim 7 wherein the contaminated impurities are at least one selected from the group consisting of the compound (1), an enantiomer of the compound (2), a 3-hydroxy nitrogen-containing compound represented by the following formula (3);

[chemical formula 17]

wherein, $R^1$ and n are as defined above, and a dehydro nitrogen-containing compound represented by the following formula (4);

[chemical formula 18]

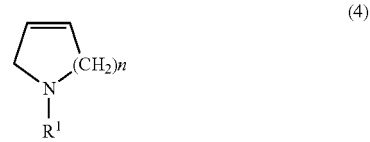

wherein, $R^1$ and n are as defined above.

9. The process for the production according to claim 7 wherein the organic solvent is at least one selected from the group consisting of methanol, ethanol, isopropanol, ethyl acetate, n-propyl acetate, isopropyl acetate, tetrahydrofuran, methyl tert-butyl ether, acetone, acetonitrile, toluene, hexane, heptane and methylcyclohexane.

10. The process for the production according to claim 7 wherein the acid is hydrogen chloride, hydrogen bromide, acetic acid, methanesulfonic acid, or p-toluenesulfonic acid.

11. A process for the production of an optically active 1-protected-3-aminopyrrolidine derivative represented by the following formula (6);

[chemical formula 19]

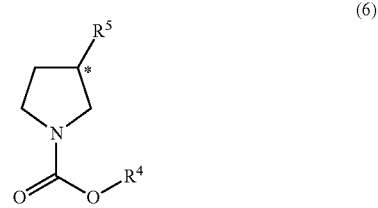

wherein $R^4$ represents an alkyl group having 1 to 20 carbon atoms which may have a substituent, an alkenyl group having 2 to 20 carbon atoms which may have a substituent, an aryl group having 6 to 20 carbon atoms which may have a substituent, or an aralkyl group having 7 to 20 carbon atoms which may have a substituent; * represents an asymmetric carbon atom; and $R^5$ is an amino group, a methylamino group, an ethylamino group, or a dimethylamino group, in which the position 3 is sterically inverted from the starting material, the process comprising allowing an optically active 1-protected-3-(sulfonyloxy)pyrrolidine derivative represented by the following formula (5);

[chemical formula 20]

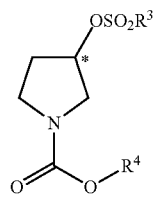
(5)

wherein, $R^3$ represents an alkyl group having 1 to 20 carbon atoms which may have a substituent, an aryl group having 6 to 20 carbon atoms which may have a substituent, or an aralkyl group having 7 to 20 carbon atoms which may have a substituent; and * and $R^4$ are as defined above, to react with ammonia, methylamine, ethylamine, or dimethylamine in the presence of at least one selected from the group consisting of methanol, ethanol, n-propanol and isopropanol at a temperature of less than 110° C. and under a pressure of 9 barr or less.

12. The process for the production according to claim 11 wherein the compound (5) is produced by catalytic reduction of an optically active 1-benzyl-3-(sulfonyloxy)pyrrolidine derivative represented by the following formula (7);

[chemical formula 21]

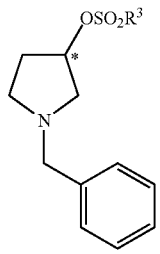
(7)

wherein, * and $R^3$ are as defined above, in the presence of an acid anhydride represented by the following formula (8);

[chemical formula 22]

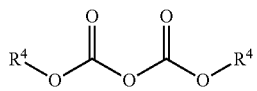
(8)

wherein, $R^4$ is as defined above.

13. The process for the production according to claim 11 wherein $R^3$ is a methyl group, an ethyl group, a trifluoromethyl group, a p-methylphenyl group or a p-chlorophenyl group.

14. The process for the production according to claim 11 wherein $R^4$ is a methyl group, an ethyl group, a n-propyl group, an isopropyl group, a tert-butyl group, or a benzyl group.

15. The process for the production according to claim 11 wherein $R^3$ is a methyl group, and $R^4$ is a tert-butyl group.

16. A process for the production of a salt of an optically active 1-protected-3-aminopyrrolidine derivative comprising: forming a salt from an acid and the compound (6) produced by the process according to claim 11; and crystallizing from an organic solvent, thereby obtaining the salt as a crystal while leaving contaminated impurities in the mother liquid.

17. The process for the production according to claim 16 wherein the contaminated impurities are at least one selected from the group consisting of the compound (5), an enantiomer of the compound (6), a compound represented by the following formula (9);

[chemical formula 23]

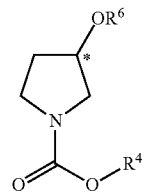
(9)

wherein, * and $R^4$ are as defined above; $R^6$ represents a methyl group, an ethyl group, a n-propyl group, or an isopropyl group, and a compound represented by the following formula (10);

[chemical formula 24]

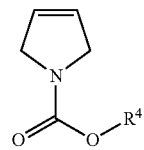
(10)

wherein, $R^4$ is as defined above.

18. The process for the production according to claim 16 wherein the organic solvent is at least one selected from the group consisting of methanol, ethanol, isopropanol, ethyl acetate, n-propyl acetate, isopropyl acetate, tetrahydrofuran, methyl tert-butyl ether, acetone, acetonitrile, toluene, hexane, heptane and methylcyclohexane.

19. The process for the production according to claim 16 wherein the acid is hydrogen chloride, hydrogen bromide, acetic acid, methanesulfonic acid, or p-toluenesulfonic acid.

* * * * *